US005989814A

United States Patent [19]
Frankel et al.

[11] Patent Number: 5,989,814
[45] Date of Patent: Nov. 23, 1999

[54] SCREENING METHODS IN EUCARYOTIC CELLS

[75] Inventors: Allan Frankel, Mill Valley; Ruoying Tan, San Francisco, both of Calif.

[73] Assignee: Reagents of the University of California, Oakland, Calif.

[21] Appl. No.: 08/847,176

[22] Filed: Apr. 1, 1997

[51] Int. Cl.$^6$ .............................. C12Q 1/68; C12N 1/19; C12N 15/63; C07H 21/02

[52] U.S. Cl. .............................. 435/6; 435/4; 435/172.2; 435/172.3; 435/240; 435/7.31; 435/70; 435/254.21; 536/23.1; 536/24.1; 536/23.4; 536/24.3

[58] Field of Search .............................. 435/4, 6, 172.2, 435/172.3, 240, 70, 7.31, 697, 320.1, 254.21; 536/23.1, 24.3, 23.4, 24.1

[56] References Cited

U.S. PATENT DOCUMENTS

| | | | |
|---|---|---|---|
| 4,608,339 | 8/1986 | Yoakum et al. | 435/172.2 |
| 5,610,015 | 3/1997 | Wickens et al. | 435/6 |
| 5,637,463 | 6/1997 | Dalton et al. | 435/6 |
| 5,683,899 | 11/1997 | Stuart | 435/172.2 |
| 5,695,941 | 12/1997 | Brent et al. | 435/6 |

OTHER PUBLICATIONS

Lufkin et al, "Identification by cell fusion of gene sequences that interact with positive trans–acting factors", Science 237:283–286, Jul. 1987.

Nonet et al, "Introduction of YACs containing a putative mammalian replication origin into mammalian cells can generate structures that replicate autonomously", Somatic Cell and Molecular Genetics 19(2):171–192, 1993.

Allen James et al., "Finding Prospective Partners in the Library: the Two–Hybrid System and Phage Display Find a Match," in *Trends Biochem. Sci.*, vol. 20, pp. 511–516, (Dec. 1995).

Felgner Philip L. et al., "Lipofection: A Highly Efficient, Lipid–Mediated DNA–Transfection Procedure," in *Proc. Natl. Acad. Sci.*, USA, Biochemisty part, vol. 84, pp. 7413–7417, (Nov. 1987).

Fouts Derrick E. et al., "Improved Method for Selecting RNA–Binding Activities in Vivo," in *Nucleic Acids Res*, vol. 24, No. 8, pp. 1582–1584, 1996.

Harada Kazuo et al., "Selection of RNA–Binding Peptides in Vivo," in *Nature*, vol. 380, pp. 175–179, (Mar. 14, 1996).

Jain CHaitanya et al., "A Structural MO&1 for the HIV–1 Rev–RRE Complex Deduced from Altered Specificity Rev Variants Isolated by a Rapid Genetic Strategy," in *Cell*, vol. 87, pp. 115–125, (Oct. 4, 1996).

Kinsella Todd M. et al., "Episomal Vectors Rapidly and Stably Produce High–Titer Recombinant Retrovirus," in *Human Gene Therapy*, vol. 7, pp. 1405–1413, (Aug. 1, 1996).

Kitamura Toshio et al., "Efficient Screening of Retroviral cDNA Expression Libraries," *Proc. Natl. Acad. Sci.*, USA, Biochemistry part, vol. 92, pp. 9146–9150, (Sep. 1995).

Rassoulzadegan Minoo et al., "High Frequency of Gene Transfer After Fusion Between Bacteria and Eukaryotic Cells," in *Nature*, vol. 295, pp. 257–259, (Jan. 21, 1982).

Sandri–Goldin Rozanne et al., "High–Frequency Transfer of Cloned Herpes Simplex Virus Type 1 Sequences to Mammalian Cells by Protoplast Fusion," in *Molecular and Cellular Biology*, vol. 1, No. 8, pp. 743–752, (Aug. 1981).

Schaffner Walter, "Direct Transfer of Cloned Genes From Bacteria to Mammalian Cells," in *Proc. Natl. Acad. Sci.*, USA, vol. 77, No. 4, Genetics part, pp. 2163–2167, (Apr. 1980).

Seed Brian et al., "Molecular Cloning of the CD2 Antigen, the T–Cell Erythrocyte Receptor, by a Rapid Immunoselection Procedure," in *Proc. Natl. Acad. Sci.*, USA, vol. 84, Immunology part, pp. 3365–3369, (May 1987).

Seed Brian, "Developments in Expression Cloning," in *Curr. Op. Biotechnol.*, vol. 6, Current Opinion in Biology, pp. 567–573, 1995.

Wilhelm et al., "A One–Hybrid System for Detecting RNA–Protein Interactions," in *Genes to Cells*, vol. 1, pp. 317–323, 1996.

Yates John L. et al., "Stable Replication of Plasmids Derived from Epstein–Barr Virus in Various Mammalian Cells," in *Nature*, vol. 313, pp. 812–815, (Feb. 28, 1985).

Li et al, "Isolation of ORC6, a component of the yeast origin recognition complex by a one–hybrid system", Science 262:1870–1874, Dec. 1993.

Wilhelm et al, "A one–hybrid system for detecting RNA–protein interactions", Genes to Cells, 1(3):317–23 Abstract only, Mar. 1996.

*Primary Examiner*—Jeffrey Fredman
*Attorney, Agent, or Firm*—Townsend & Townsend & Crew

[57] ABSTRACT

The invention provides new methods for screening libraries of peptides and other compounds for a desired property in eucaryotic cells. The methods are premised, in part, on the unexpected observation that the contents of procaryotic or lower eucaryotic cells, such as yeast, can be transferred to recipient eucaryotic cells in an essentially clonal manner by protoplast fusion of the respective cells. Applications of the methods include screening peptides in eucaryotic cells substantially incapable of episomal replication of transferred nucleic acid fragments; screening in eucaryotic cells peptides or secondary metabolites produced in procaryotic cells; and screening a library of peptides for capacity to bind a selected RNA in eucaryotic cells.

33 Claims, 10 Drawing Sheets

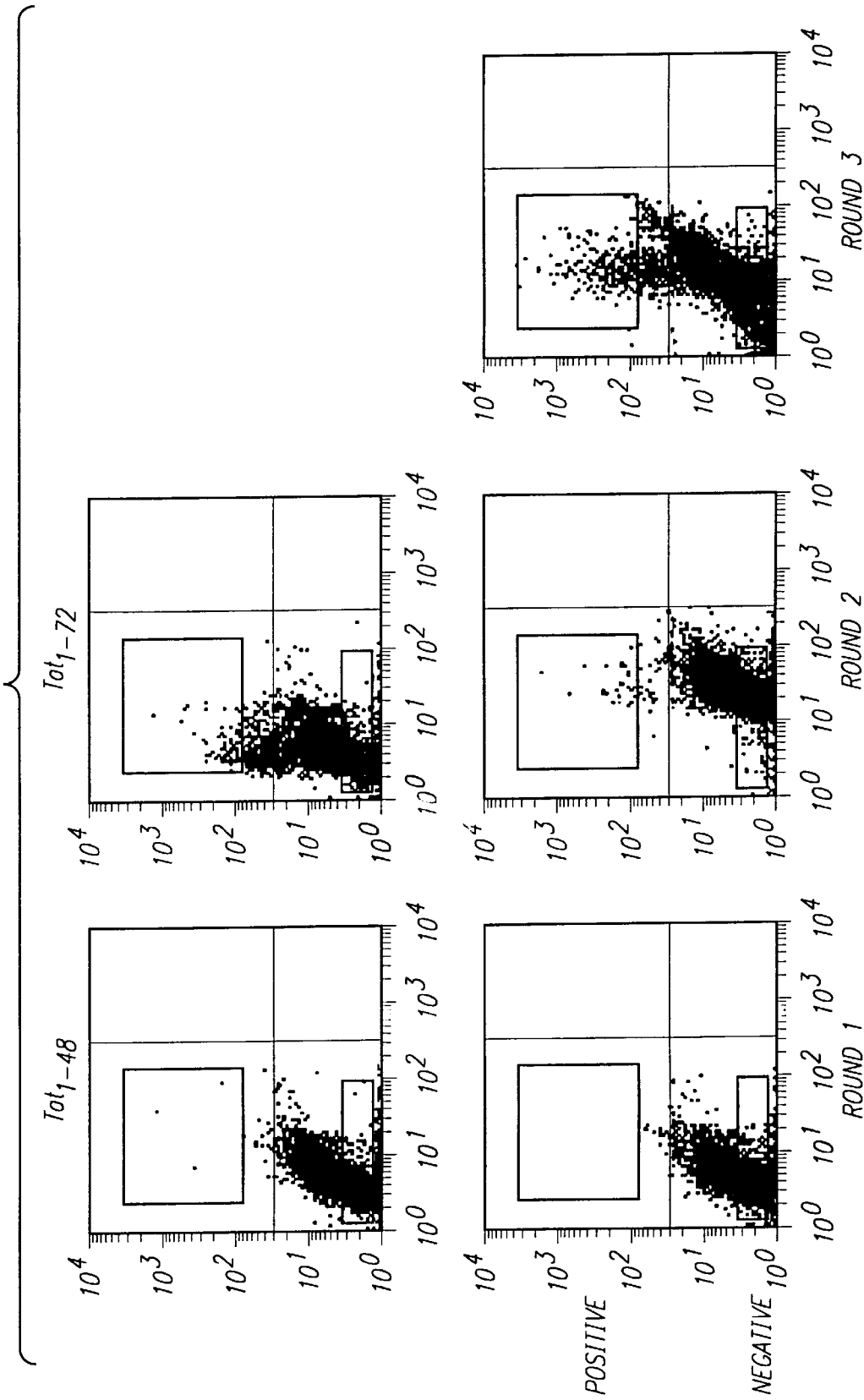

FIG. 6A

|   | U | C | A | G |
|---|---|---|---|---|
| U | F L | S | Y TERM | C TERM W |
| C | L | P | H Q | R |
| A | I M | T | N K | S R |
| G | V | A | D E | G |

(right side column labels: U C A G / U C A G / U C A G / U C A G)

FIG. 6B

AAAARRRRRRRRRRRRRAAAAR   Arg$_{14}$

AAAATRQARRNRRRRRRAAAAR   Rev$_{14}$

AAAA▓R▓▓RR▓RRRRRRRAAAAR   library

```
                        40
                         ↓
Rev₁₄    AAAA  TRQARRNRRRRRRRR  AAAAR
Arg₁₄    AAAA  RRRRRRRRRRRRRR   AAAAR
─────────────────────────────────────
                         ↓
clone 1  AAAA  RRRHRRQRRRRRRR   AAAAR
clone 2  AAAA  GRRRRRQRRRRRRR   AAAAR
clone 3  AAAA  GRRARRRRRRRRQSCRRKMTRD
clone 4  AAAA  RRRERRRRRRRRQSCRRKMTRD
clone 5  AAAA  GRQGRRRRRRRRQSCRRKMTRD
clone 6  AAAA  GRRRRRQRRRRRRKLPPQDDSRLVDPDPPGFSV
─────────────────────────────────────
                         ↓
         AAAA  QRRRRRQRRRRRRR   AAAAR
         AAAA  GRRRRRQRRRRRRR   AAAAR
         AAAA  QRRKRRQRRRRRRR   AAAAR
         AAAA  GRSARRNRRRRRRR   AAAAR
         AAAA  QRRARRQRRRRRRR   AAAAR
         AAAA  SRRRRRQRRRRRRR   AAAAR
         AAAA  RRAKRRDRRRRRRR   AAAAR
         AAAA  RRQRRRARRRRRRR   AAAAR
         AAAA  SRRRRRQRRRRRRR   AAAAR
         AAAA  GRRQRRQRRRRRRR   AAAAR
         AAAA  GRRQRRRRRRRRRR   AAAAR
         AAAA  RRRRRRQRRRRRRR   AAAAR
         AAAA  GRKGRRERRRRRRR   AARKMTRD
         AAAA  GRGERRRRRRRRQSCRRKMTRD
         AAA   GRETRRQRRRRRQSCRRKMTRD
```

FIG. 7

SCREENING METHODS IN EUCARYOTIC CELLS

CROSS-REFERENCE TO RELATED APPLICATION

Commonly owned, copending application Ser. No. 08/442,461, filed May 17, 1995, describes related subject matter and is incorporated by reference in its entirety for all purposes.

STATEMENT OF GOVERNMENT INTEREST

This invention was made with Government support under Grant Nos. AI29135 and GM47478 awarded by the National Institutes of Health. The Government has certain rights in this invention.

BACKGROUND

In recent years, a number of in vitro methods have been developed for screening polypeptides for a desired binding specificity. For example, the phage display technique screens polypeptides displayed as a coat protein from a bacteriophage. See, e.g., Dower et al., WO 91/17271; McCafferty et al., WO 92/01047.; Ladner, U.S. Pat. No. 5,223,409 (incorporated by reference in their entirety for all purposes). Another in vitro screening method has been developed for isolating nucleic acid sequences that bind to proteins. See Gold et al., U.S. Pat. No. 5,270,163.

In vivo methods for screening libraries have also been reported. Such methods usually detect protein-protein or protein-nucleic acid interactions using reporter constructs to identify active members of a library (Allen et al., 1995). For example, a yeast three-hybrid system has been used to identify a cDNA encoding a protein that binds the 3' end of histone mRNAs, and bacterial reporter systems based on transcriptional antitermination or translational inhibition have been used to screen RNA-binding libraries in several different contexts (Fouts et al., 1996; Harada et al., 1996, Jain et al., 1996; Wilhelm et al., 1996). These methods are especially useful for screening cDNA expression libraries and, arguably, mimic physiological conditions more closely than the in vitro methods. Further, such methods allow screening for physiological or functional properties as distinct from merely binding activity. In vivo screens are usually performed in bacteria or fungi, such as yeast, because of high transformation efficiencies and because it is possible to transform many cells and obtain individual clones.

Because many libraries are screened to obtain therapeutic compounds and mammalian cells more closely simulate the environment of intended therapeutic use than procaryotic, yeast or in vitro screens, it would be desirable to screen libraries in mammalian cells. For example, protein folding or posttranslational modification of some peptides may be different in eucaryotic and procaryotic cells. Screening in mammalian cells is, however, generally more difficult than screening in procaryotes because: (1) transfection efficiencies are lower; (2) unlike bacteria or yeast where plasmid segregation results in clonal colonies, transfection of mammalian cells is believed to involve the uptake of a large population of plasmids; (3) in general, eucaryotic cells do not support episomal replication of plasmids, (4) establishment of stable eucaryotic cell lines with integrated vector is laborious and may not result in expression of many library members, (5) recovery of a selected vector from eucaryotic cells can be difficult.

Some progress has been reported to address these difficulties. Transfection efficiencies have been reported to be improved using liposomes, protoplasts, or retroviruses as delivery vehicles (Schaffner, 1980; Sandri-Goldin et al, 1981; Rassoulzadegan et al., 1982, Felgner et al., 1987; Kitamura et al., 1995). Selected plasmids have been reported to have been enriched from pools introduced into a cell by transfection by subdividing active pools and performing multiple rounds of enrichment (Seed, 1995). Further, plasmid recovery has been reported to be improved using episomally replicating plasmids containing SV40, polyoma, or Epstein Barr Virus (EBV) origins in specific cell types supporting episomal replication of such plasmids (Yates et al., 1985; Seed et al., 1987; Kinsella et al., 1996). Thus, for example, a cDNA expression cloning strategy has been reported by Seed et al., 1987 using plasmids containing an SV40 origin. This origin allows the plasmids to replicate episomally to high levels in COS cells, which express large T-antigen. SV40-vector libraries, were introduced into COS cells by protoplast fusion, the libraries were amplified episomally, and cells expressing the CD2 surface antigen were isolated by panning with antibodies, and amplified vectors were recovered from Hirt supernatants of the isolated cells.

Despite some progress as noted above, difficulties and limitations remain in screening libraries in eucaryotic cells, and improved methods are needed.

DEFINITIONS

A specific binding affinity of one entity for another refers to a dissociation constant $\leq 10\,\mu M$, preferably $\leq 100$ nM and most preferably $\leq 10$ nM. RNA peptides isolated by the claimed methods bind one (or more) RNA binding sites more strongly (i.e., at least 5-fold, 10-fold, 100-fold or 1000-fold) than others. Dissociation constants as low as 1 nM, 1 pM or 1 fM are possible for protein-RNA binding.

A DNA segment is operably linked when placed into a functional relationship with another DNA segment. For example, a promoter is operably linked to a coding sequence if it stimulates the transcription of the sequence. Generally, DNA sequences that are operably linked are contiguous, and in the case of two amino acid coding sequences, both contiguous and in reading phase. Linking is accomplished by ligation at convenient restriction sites or at adapters or linkers inserted in lieu thereof.

The term nucleic acid include RNA, DNA and peptide nucleic acids, single-stranded or double-stranded.

Peptide or polypeptide refers to a polymer in which the monomers typically are alpha-(L)-amino acids joined together through amide bonds. Peptides are at least two and usually three or more amino acid monomers long. The term protein is used to refer to a full-length natural polypeptide or a synthetic polypeptide that is sufficiently long to have a self-sustaining secondary structure (e.g., α-helix or β-pleated sheet) and at least one functional domain.

Random peptide refers to an oligomer composed of two or more amino acid monomers and constructed by a means with which one does not entirely preselect the complete sequence of a particular oligomer.

A random peptide library refers not only to a set of recombinant DNA vectors (also called recombinants) that encodes a set of random peptides, but also to the set of random peptides encoded by those vectors, as well as the set of fusion proteins containing those random peptides. Random peptide libraries frequently contain as many as $10^6$ to $10^{12}$ different compounds.

The lefthand direction of a polypeptide is the amino terminal direction and the righthand direction is the carboxy-terminal direction, in accordance with convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand which are 5' the RNA transcript are referred to as "upstream sequences"; sequence regions on the DNA strand which are 3' to the RNA transcript are referred to as "downstream sequences."

A variant of a natural polypeptide usually exhibits at least 20%, and more usually at least 50%, sequence similarity to the natural polypeptide. The term sequence similarity means peptides have identical or similar amino acids (i.e., conservative substitutions) at corresponding positions.

The polypeptides of the present invention are obtained in a substantially pure form, typically being at least 50% weight/weight (w/w) or higher purity, and being substantially free of interfering proteins and contaminants, such as those which may result from expression in cultured cells. Preferably, the peptides are purified to at least 80% w/w purity, more preferably to at least 95% w/w purity. For use in pharmaceutical compositions, the polypeptide purity should be very high, typically being at least 99% w/w purity, and preferably being higher.

SUMMARY OF THE INVENTION

The invention provides methods of screening a library of nucleic acid fragments in eucaryotic cells. The library can be a natural library or a combinatorial library. In some methods, the library of nucleic acid fragment is transformed into primary cells, which are procaryotic or fungi. The primary cells are cultured under conditions in which the copy number of nucleic acid fragments is amplified to an average of at least 200 copies per transformed cell. The transformed primary cells are contacted with a population of eucaryotic cells under conditions in which outersurfaces of the transformed primary cells and eucaryotic cells fuse and contents of the transformed primary cells including at least some of the library of nucleic acid fragments are transferred to the eucaryotic cells. The nucleic acid fragments are screened in the eucaryotic cells to isolate one or more eucaryotic cells having a desired property conferred by one or more members of the library of nucleic acid fragments, an expression product thereof, or a secondary metabolite of an expression product. The one or more eucaryotic cells thus isolated are lysed releasing the one or more members of the library of nucleic acids conferring the desired property and these nucleic acids are electroporated into fresh procaryotic cells. The fresh cells are then propagated to amplify the one or more members of the library of nucleic acids, which confer the desired property. Typically, a nucleic acid fragment is isolated from the cells. Optionally, the methods can be performed in a cyclic fashion in which the amplified procaryotic cells of one cycle form the transformed primary cells in the next cycle.

In some methods, the primary cells are *E. coli*, the nucleic acid fragments are contained in a ColE1 vector, and the primary cells are cultured in the presence of an antibiotic to amplify the copy number of the library of nucleic acid fragments. In some methods, the eucaryotic cells lack capacity for episomal replication of the transferred nucleic acid fragments. In some methods, the nucleic acid fragments encode different peptides, and one or more of the peptides confers the desired property in the eucaryotic cells. In some methods, the nucleic acid fragments encode enzymes, which produce secondary metabolites in the procaryotic cells, which are transferred together with at least some of the nucleic acid fragments to the eucaryotic cells, and one or more of the secondary metabolites confers the desired property in the eucaryotic cells.

The nature of the screen depends on the desired property. In some methods, in the screening step, the eucaryotic cells contain a construct encoding a reporter enzyme operably linked to a regulatory sequence. Peptides can then confer the desired property by binding to the regulatory sequence or a transcript thereof inducing expression of the reporter enzyme. The reporter construct can be introduced into eucaryotic cells with the library of nucleic acid fragments, or can be transferred sequentially.

Some methods are used to screen expression products of a library of nucleic acid fragments or secondary metabolites thereof that are expressed in procaryotic cells or fungi. In these methods, the library of nucleic acid fragments is transformed into primary cells, which are procaryotic cells or fungi. The cells are cultured under conditions in which expression products and/or secondary metabolites of expression products are produced. The transformed cells are contacted with a population of eucaryotic cells under conditions whereby outersurfaces of the transformed procaryotic and eucaryotic cells fuse and contents of the transformed procaryotic cells including at least some of the library of nucleic acid fragments, expression products thereof and/or secondary metabolites of expression products are transferred to the eucaryotic cells. At least some eucaryotic cells receive an expression product and/or a secondary metabolite thereof and a nucleic acid fragment encoding the expression product. The eucaryotic cells are screened to isolate one or more eucaryotic cells having a desired property conferred by one or more of the expression products or one or more of the secondary metabolites produced in the primary cells. The one or more members of the library of nucleic acids ar transferred from the one or more eucaryotic cells into fresh procaryotic cells. The transformed fresh procaryotic cells are propagated to amplify the one or more members of the library of nucleic acids, which produce the one or more expression products and/or one or more secondary metabolites that confer the desired property.

Some methods are used to screen peptides for capacity to bind a selected RNA in a eucaryotic cells. Such methods entail introducing a library of nucleic acids encoding fusion proteins into a population of eucaryotic cells. Such a fusion protein comprises a peptide linked to a transcriptional inducer, the peptides varying between fusion proteins. The eucaryotic cells further comprise a construct encoding a reporter gene operably linked to a promoter from which expression is stimulated by the transcriptional inducer and an RNA binding site. The one or more fusion proteins, each comprise a peptide having specific affinity for the RNA binding site bind to the RNA binding site of the reporter construct or a transcript thereof via the peptide, and the transcriptional inducer linked to the peptide stimulates expression of the reporter gene from the promoter. One or more eucaryotic cells with stimulated expression of the reporter gene are isolated. These cells contain one or more nucleic acid fragments encoding the one or more fusion proteins comprising a peptide having specific affinity for the RNA binding site. In some such methods, the transcriptional inducer is a HIV TAT polypeptide and the promoter is a HIV LTR promoter.

BRIEF DESCRIPTION OF THE FIGURES

FIG. 5. Enrichment of positive clones in a mock library. HIV-1 LTR-GFP reporter cells were fused with a protoplast mixture containing pSV2Tat1-72 and pSV2Tat1-48 in a 1:10$^5$ ratio (Round 1). Fusions with each plasmid separately (top) were used to set sorting windows for positive and negative cells (boxes). Protoplasts made from positive cells sorted in Round 1 were fused to reporter cells (Round 2), and protoplasts made from positive cells sorted in Round 2 were again fused to reporter cells (Round 3). Individual clones from each round were analyzed by PCR, as described in the text.

FIG. 7. Sequences of selected RRE binders. Rev14 (SEQ ID NO:1) and Arg14 (SEQ ID NO:2) are shown in the top section. Clones 1–6 (SEQ ID NOS:4–9, respectively were identified by selecting for high-level GFP expression and were found in a total of 35 GFP-positive individual clones. Sequences in the bottom section (SEQ ID NOS:10, 5, 11–16, 14 and 17–22, respectively) were identified from 18 positive clones after four rounds of selection using a slightly lower sorting window.

DETAILED DESCRIPTION

I. General

Figure 1:
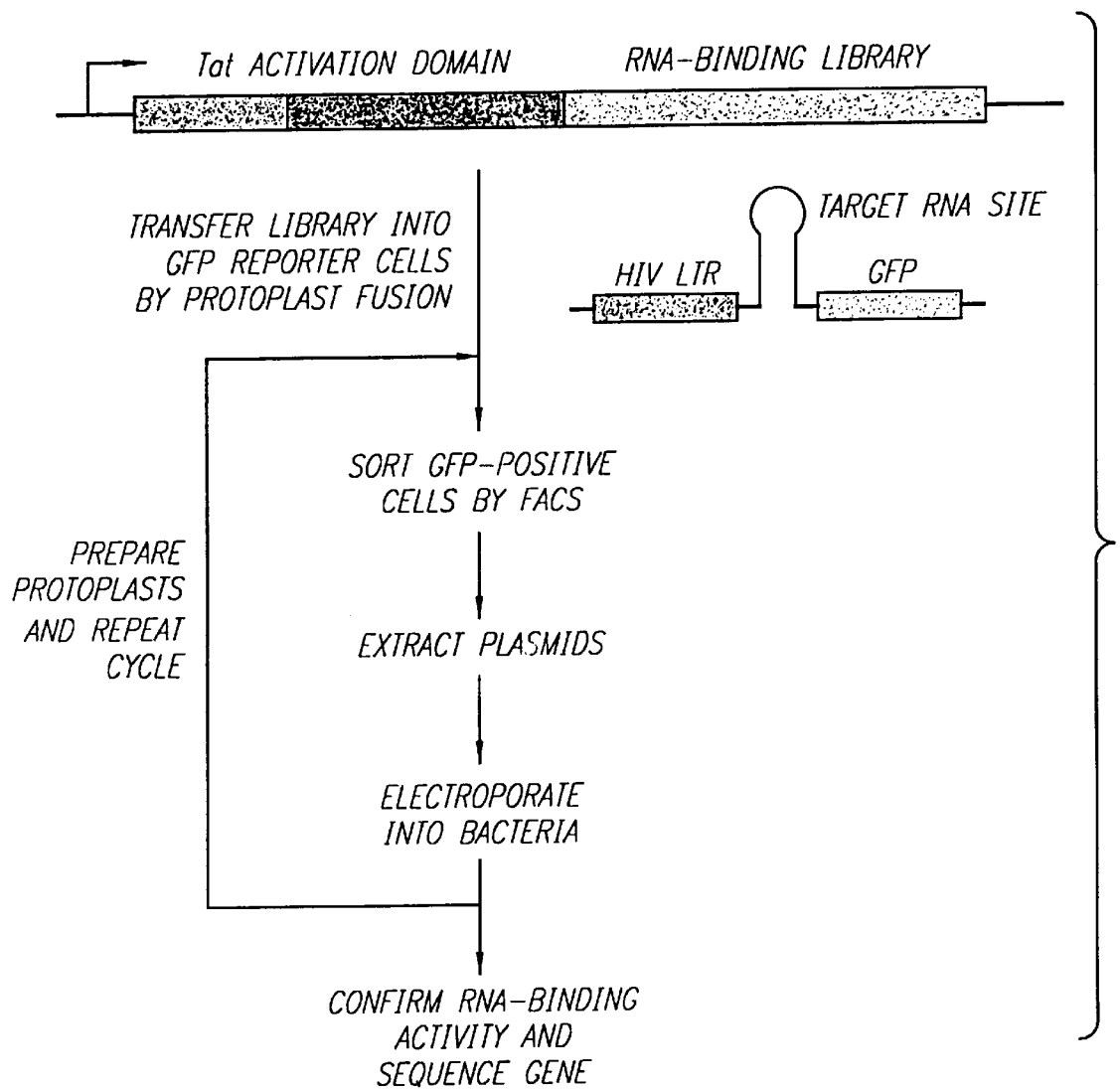
FIG. 1. Strategy for screening RNA-binding libraries. Libraries are fused to the activation domain of HIV-1 Tat (amino acids 1–48) or to full-length Tat and are delivered into stable cells containing an appropriate GFP reporter by protoplast fusion. GFP-expressing cells are isolated by FACS sorting, and plasmids are extracted by alkaline lysis and electroporated into bacteria. Protoplasts are made from the enriched population and the cycle is repeated until a large proportion of fused cells express GFP. Individual clones are tested for activity and positives are sequenced.

The invention provides new methods for screening libraries of peptides and other compounds for a desired property in eucaryotic cells. The methods are premised, in part, on the unexpected observation that the contents of procaryotic or lower eucaryotic cells, such as yeast, can be transferred to recipient eucaryotic cells in an essentially clonal manner by protoplast fusion of the respective cells. That is, when a library of protoplasts of procaryotic or lower eucaryotic cells are fused with recipient eucaryotic cells, transfer occurs by a mechanism in which most transfected recipient cells (e.g., at least 50 or 75%) have received the contents of only a single protoplast. The essentially clonal transfer pertains even when protoplasts are present in large excess over recipient cells, as is necessary to maximize the proportion of recipient cells undergoing transfection.

This result may occur because fusion is a low frequency process so that on average few protoplasts actually fuse, and/or because delivery of many plasmids from one protoplast quickly saturates the cellular DNA uptake system and prevents entry of additional plasmids. Whatever the mechanism, near-clonal delivery is advantageous for library screening because: (1) plasmids conferring a desired property are transferred to recipient cells in homogenous form and can be isolated from such cells without laborious procedures such as subdividing active pools, (2) homogenous transfer also allows for detection of weakly active members that might be missed if recipient cells received a mixture of plasmids, and (3) false positives and negatives caused by nonactive members delivered to the same cell as an active member of a library are reduced.

The feasibility of clonal transfer can be exploited in several methods for screening libraries of nucleic acids, peptides or other compounds in higher eucaryotic cells. Such methods begin by transforming a library of nucleic acid fragments into primary cells, usually procaryotic. The transformed cells are then usually cultured under conditions that allow amplification of the molecule sought to be screened. Preferably, the molecule is amplified to at least 100, 200, 500 or 1000 copies per cell. For example, nucleic acids cloned in ColE1 vectors can be amplified to a copy number of over 1000 per cell by treating the cell culture with an antibiotic that inhibits protein synthesis. Peptides encoded by nucleic acids or secondary metabolites of such peptides can be amplified by culturing the cells under appropriate nutritional conditions. After amplification, protoplasts are formed from primary cells and the protoplasts are contacted with recipient eucaryotic cells under conditions in which the cells fuse and the contents of the primary cells are transferred to the recipient cells.

As noted, transfer occurs in an essentially clonal fashion such that most transfected cells receive the contents of a single protoplast. A transfected eucaryotic cell thus typically receives multiple copies of a member of the nucleic acid fragment library together with an expression product of the nucleic acid fragment, and in some instances, a secondary metabolite of the expression product. Transfected eucaryotic cells are allowed to recover from the fusion protocol, and are then screened for a desired property conferred directly or indirectly by a nucleic acid library member. Properties are conferred indirectly if they are conferred by an expression product of a nucleic acid library member or a secondary metabolite of an expression product.

Eucaryotic cells having the desired property are isolated from other cells, for example, by FACS sorting. Nucleic acids are recovered from the isolated cells and transferred, preferably by lysis and electroporation, to further procaryotic cells. The cells are then cultured to amplify the nucleic acids conferring the desired property. Preferably, the method is performed in a cyclic fashion with the transformed procaryotic cells containing nucleic acid conferring the desired property being used to form protoplasts for fusion with further eucaryotic cells. Eventually, nucleic acid fragments conferring the desired property, their expression products or secondary metabolites are characterized, e.g., by sequencing an isolated nucleic acid fragment.

The methods described above have general applicability for efficient screening of libraries in higher eucaryotic cells. However, some applications are particularly noteworthy. For example, the methods can be used to screen nucleic acid libraries in eucaryotic cell types that do not support episomal replication of transferred nucleic acid. Episomal replication is not needed because nucleic acids can be amplified to high copy number in the primary cells before transfer to eucaryotic cells occurs. Thus, transfected eucaryotic cells receive sufficient copies of a nucleic acid library member to allow screening and recovering after screening to be effected without amplification of the copy number of the library member in the eucaryotic cells.

Another application of the methods resides in the screening of polypeptides or secondary metabolites that are synthesized in the primary cells before transfer to the eucaryotic cell. As previously noted, expression products and/or secondary metabolites of a nucleic acid library member can be transferred to eucaryotic cells together with corresponding nucleic acid members encoding the expression products. Thus, protoplast transfer effectively preserves genetic linkage during screening between a nucleic acid and peptide encoded by it or a secondary metabolite thereof, in a manner analogous to a phage-display system. Transferred peptides or secondary metabolites are screened for a desired property in the eucaryotic cells. Nucleic acid members are then recovered from cells having the desired property, and the identity of peptides or secondary metabolites having the desired property can be determined indirectly, by sequencing the nucleic acid or allowing the nucleic acid to be expressed to produce a secondary metabolite, which can then be characterized by conventional methods.

A further application of the above methods resides in screening libraries of peptides for capacity to bind to a selected RNA target in eucaryotic cells. For example, such methods can be used to identify peptides that bind tightly to an RNA sequence of an RNA virus and thereby inhibit replication or expression of the virus. Peptides are screened linked to a transcriptional inducer as a fusion protein. Peptide having activity for a selected RNA binding site, bind to a reporter construct containing that site and thereby allow the transcriptional inducer to stimulate expression of a reporter gene on the reporter construct.

II. Cell Types Usable in the Methods

The primary cells used for protoplast fusion in the above methods are usually procaryotic but can also be from lower eucaryotes such as yeast. The cells should be transformable at high frequency and capable of forming protoplasts. The cells should preferably also be capable of supporting a high level of expression of the molecular species sought to be screened in mammalian cells. Typically, the cells types are those commonly used in genetic engineering such as Bacillus, *Escherichia coli*, Pseudomonas, Salmonella, actinomycetes, and yeast.

Eucaryotic cells suitable for screening are usually cell types that can be grown in tissue culture such as mammalian or plant cells. Suitable cells include those from, e.g., mouse, rat, hamster, primate, and human, both cell lines and primary cultures. Such cells include stem cells, including embryonic stem cells and hemopoietic stem cells, zygotes, fibroblasts, lymphocytes, Chinese hamster ovary (CHO), mouse fibroblasts (NIH3T3), kidney, liver, muscle, and skin cells. Other eucaryotic cells of interest include plant cells, such as maize, rice, wheat, cotton, soybean, sugarcane, tobacco.

III. Libraries

The libraries of nucleic acids screenable by the methods can be natural cDNA or genomic libraries or can be combinatorial libraries in which one or more positions in library members is varied in a systematic manner between library members. Some libraries have members which encode short random peptides about 6–25 amino acids long. Other libraries encode variant forms of a naturally occurring protein.

In some methods, library members encode one or more enzymes which alone, or together with other cellular enzymes, catalyze the production of a secondary metabolite. In this situation, library members encode variant forms of an enzyme or cluster of enzymes, and variation between the enzymes or clusters of enzymes in different library members causes variation in secondary metabolites produced in cells containing the enzymes. Secondary metabolites include antibiotics, polyketides, isoprenoids, vitamins, dyes, non-ribsomomally-synthesized peptides, enzymically modified peptides, and amino acids. Strategies for mutation of genes encoding enzymes involved in secondary metabolite production are described by Hutchinson, *Bio/Technology* 12, 375–308 (1994)). Sources of cloned genes encoding enzymes involved in antibiotic synthesis are reviewed by e.g., Piepersberg, *Crit. Rev. Biotechnol.* 14, 251–285 (1994); Chater, *Bio/Technology* 8, 115–121 (1990). Examples of cloned isoprenoid synthesis genes include trichodiene synthase from *Fusarium sprorotrichioides*, pentalene synthase from Streptomyces, aristolochene synthase from *Penicillium roquefortii*, and epi-aristolochene synthase from *N. tabacum* (Cane, in *Genetics and Biochemistry of Antibiotic Production* (ed. Vining & Stuttard, Butterworth-Heinemann, 1995), pp. 633–655. Production of secondary metabolites biodegradable plastic polyhydroxybutarate (PHB), and the polysaccharide xanthan gum is reviewed by Cameron et al., *Applied Biochem. Biotech.* 38, 105–140 (1993). Genes encoding enzymes that catalyze the conversion of glucose to 2,5-keto-gluconic acid, and that product to 2-keto-L-idonic acid, the precursor to L-ascorbic acid are reviewed by Boudrant, *Enzyme Microb. Technol.* 12, 322–329 (1990)).

In other situations, library members encode RNA molecules which are to be screened in eucaryotic cells. For example, the methods can be used to screen a library RNA molecules to identify those with affinity for a specific protein target.

Typically, library members are cloned in a vector allowing episomal replication and/or expression of library members in the primary cells. In some methods, the vector contains a ColE1 origin of replication allowing amplification of vector copy number to high levels (ca. 3000 copies per cell) by treatment with an antibiotic that inhibits protein synthesis. The vector may, but need not, contain a second origin of replication to allow subsequent episomal replication in higher eucaryotic cells. If such an origin is desired, an SV40 origin allows episomal replication in COS cells, and an EBV origin together with a coding sequence for EBNA-1 protein allows replication in a variety of cell types, but copy numbers are lower than with SV40-based plasmids.

Libraries are constructed by cloning an oligonucleotide which contains the variable region of library members (and any spacers and nonvariable framework determinants) into the selected cloning site. Using known recombinant DNA techniques (see generally, Sambrook et al., *Molecular Cloning, A Laboratory Manual,* 2d ed., Cold Spring Harbor Laboratory Press, Cold Spring Harbor, N.Y., 1989, incorporated by reference in its entirety for all purposes), an oligonucleotide may be constructed which, inter alia, removes unwanted restriction sites and adds desired ones, reconstructs the correct portions of any sequences which have been removed (such as a correct signal peptidase site, for example), inserts the spacer conserved or framework residues, if any, and corrects the translation frame (if necessary) to produce a fusion protein. A portion of the oligonucleotide will generally contain one or more variable region domain(s) and the spacer or framework residues. The sequences are ultimately expressed as peptides (with or without spacer or framework residues). The variable region domain of the oligonucleotide comprises the source of the library.

The size of the library varies according to the number of variable codons, and hence the size of the peptides, which are desired. Generally the library will be at least about $10^4$ or $10^6$ members, usually at least $10^7$, and typically $10^8$ or more members. For example, given the current efficiency of protoplast delivery (10–20% of cells receive library members), the ability to recover about one procaryotic colony per sorted eucaryotic cell, and a practical limit of FACS sorting ($10^7$–$10^8$ cells), it is possible to screen libraries of $10^6$–$10^7$ complexity with reasonable confidence, a level sufficient to clone low-abundance cDNAs.

Nucleic acids are introduced into primary cells by standard methods depending on the cell type. Electroporation is preferred for generating large libraries in many bacterial cell types.

IV. Protoplast Fusion

Protoplast fusion is a method for transferring nucleic acids and other components from a procaryotic or lower eucaryotic cell (e.g., fungus) to a higher eucaryotic cell that occurs at high frequency. A protoplast results from the removal from a cell of its cell wall, leaving a membrane-bound cell that depends on an isotonic or hypertonic medium for maintaining its integrity. If the cell wall is partially removed, the resulting cell is strictly referred to as a spheroplast and if it is completely removed, as a protoplast. However, here the term protoplast includes spheroplast unless otherwise indicated.

The method involved two steps: conversion of procaryotes or the lower eucaryote to protoplasts and the fusion of the protoplasts to the higher eucaryotic cells. Protoplast fusion was first described by Shaffner et al., *Proc. Natl. Acad. Sci. USA* 77, 2163 (1980) and other exemplary procedures are described by Yoakum et al., U.S. Pat. No. 4,608,339, Takahashi et al., U.S. Pat. No. 4,677,066 and Sambrooke et al., supra at Ch. 16. The first step is typically effected by digestion of cell walls with lysozyme in a 10–20% sucrose, 50 mM EDTA buffer. Conversion of rod-shaped cells to spherical protoplasts can be monitored by phase-contrast microscopy. Protoplasts are then centrifuged onto a layer of eucaryotic cells, usually with the protoplasts in excess (up to about 100, 1000 or 10,000-fold). PEG is added to promote cell fusion. The transfected eucaryotic cells are sometimes propagated in antibiotic media to kill any bacterial cells surviving protoplast fusion. A method of cell fusion employing electric fields has also been described. See Chang U.S. Pat. No. , 4,970,154.

V. Screening in Higher Eucaryotic Cells

After protoplast fusion, nucleic acid library members, their RNA or peptide expression products, or secondary metabolites are screened for a desired property. Examples of desired properties that can be screened for include encoding a cell surface antigen, a capacity to bind to a selected target, which can be a cellular protein or nucleic acid, a capacity to stimulate or inhibit a cellular process, toxicity to the recipient cell. The nature of the screen depends on the desired property. Libraries can be screened for a member encoding a cell surface protein of interest by screening cells with an antibody or other binding partner of the surface protein. Dead cells conferred by a toxic expression product of a transferred sequence can be distinguished by trypan blue exclusion. Other screens detect a new enzymic activity conferred by a library member or a capacity of the cells to grow without an otherwise essential nutrient.

Screens for a specific binding affinity or for effect on a cellular metabolic process can often be devised in which active library members cause enhanced expression of a reporter gene from a reporter construct. The reporter gene can be any gene that confers a selectable or screenable property when it is expressed. Suitable reporter genes include the β-galactosidase gene, antibiotic resistance genes, such as CAT, and genes having a fluorescent expression product, such as the green fluorescent protein gene.

An example of such a reporter system to screen peptides for RNA binding activity is discussed in detail below. A reporter system for screening peptide-peptide binding is described by Fearon et al., *Proc. Natl. Acad. Sci. U.S.A.* 89, 7958–7962 (1992). Peptide-peptide binding is identified by reconstitution of the functional activity of the yeast transcriptional activator GAL4 and the resultant transcription of a GAL4-regulated reporter gene. Reconstitution of GAL4 function results from specific interaction between two chimeric proteins, one of which contains the DNA binding domain of GAL4, and the other contains a transcriptional activation domain. Transcription of the reporter gene occurs if the two chimeric proteins can form a complex that reconstitutes the DNA binding and transcriptional activation functions of GAL4. A reporter system for screening DNA-peptide binding interactions has been described by Li & Herskowitz, *Science* 262, 1870–4 (1993).

In screening methods employing a reporter construct, the construct can be introduced into the higher eucaryotic cells before protoplast fusion. The construct is typically integrated into the cellular genome as a stable cell line. Alternatively, the reporter construct can be introduced into recipient higher mammalian cells in the course of protoplast fusion. In this situation, the construct is first introduced into the primary cells from which protoplasts are made and is transferred to the higher eucaryotic cells with other components of the primary cells.

In general, transferred nucleic acid library members can be screened without substantial replication (e.g., no more than about a 2- or 5-fold increase in average copy number) of the library members in eucaryotic cell. Replication is not necessary because the essentially clonal nature of protoplast fusion can transfer sufficient copies of nucleic acid library members for screening without replication. Also, it is not essential that library members be expressed in recipient higher eucaryotic cells, as expression products of the nucleic acids and/or secondary metabolites are transferred with the nucleic acids. For most secondary metabolites, and some peptides, expression is only possible in procaryotic cells.

VI. Recovery of Library Members from Selected Eucaryotic Cells

Library members are recovered from eucaryotic cells surviving selection for transfer to further procaryotic cells. Library members can sometimes be recovered in small amounts from Hirt supernatants of cells. However, higher yields are obtained if library members are released from eucaryotic cells by an alkaline lysis procedure. Library members are then transformed into procaryotic cells, usually, *E. coli* for amplification. Transformation is preferably by electroporation for highest efficiency transformation of what are often small amounts of DNA, particularly, if no replication was performed in the eucaryotic cells. The number of different library members recovered may range from 1, 10, 50, 500, to 10,000 or more. Usually, the library members are recovered from a population of cells surviving selection without clonal isolation of individual cells.

Following electroporation, the procaryotic cells are cultured to amplify selected library members. Often the library members are subjected to further round(s) of enrichment using the same principles as before. That is, the procaryotic cells bearing selected library members are used to make protoplast for another rounds of screening in eucaryotic cells. Procaryotic cells can also be clonally isolated before performing subsequent rounds of screening. Eventually, selected nucleic acids are subject to further characterization. When the nucleic acids encode peptides, further characterization entails sequencing the nucleic acid and then resynthesizing the peptide from the nucleic acid sequence, in similar fashion to phage display methods. The same analysis hold if the nucleic acids encode RNA molecules. In situations, where the nucleic acids encode secondary metabolites, sequencing of selected nucleic acids can be used to identify enzyme(s) that lead to production of a secondary metabolite having a desired activity. The secondary metabolite itself can be recovered from cells expressing these nucleic acids, and characterized directly by conventional chemical methods such as infrared or mass spectrophotometry.

VII. Screening for RNA Binding Peptides

1. RNA Binding Protein and Recognition Sequences

Natural RNA binding proteins often have one domain responsible for RNA binding and other domains responsible for other functions. The domain responsible for RNA binding can sometimes be recognized by a characteristic motif. The most widely found RNA recognition sequence or binding motif is the RNP motif. The RNP motif is a 90–100 amino acid sequence that is present in one or more copies in proteins that bind pre mRNA, mRNA, pre-ribosomal RNA and snRNA. The consensus sequence and the sequences of several exemplary proteins containing the RNP motif are provided by Burd and Dreyfuss, supra. See also Swanson et al., *Trends Biochem. Sci.* 13, 86 (1988); Bandziulis et al., *Genes Dev.* 3,431 (1989); Kenan et al., *Trends Biochem. Sci.* 16, 214 (1991). The consensus motif contains two short consensus sequences RNP-1 and RNP-2. Some RNP proteins bind specific RNA sequences with high affinities (dissociation constant in the range of $10^{-8}10^{-11}$ M). Such proteins often function in RNA processing reactions. Other RNP proteins have less stringent sequence requirements and bind less strongly (dissociation constant $~10^{-6}$–$10^{-7}$ M). Burd & Dreyfuss, *EMBO J.* 13, 1197 (1994).

A second characteristic RNA binding motif found in viral, phage and ribosomal proteins is an arginine-rich motif (ARM) of about 10–20 amino acids. RNA binding proteins having this motif include the HIV Tat and Rev proteins. Rev binds with high affinity disassociation constant ($10^{-9}$ M) to an RNA sequence termed RRE, which is found in all HIV mRNAs. Zapp et al., *Nature* 342, 714 (1989); Dayton et al., *Science* 246, 1625 (1989). Tat binds to an RNA sequence termed TAR with a dissociation constant of $5\times10^{-9}$ M. Churcher et al., *J. Mol. Biol.* 230, 90 (1993). For Tat and Rev proteins, a fragment containing the arginine-rich motif binds as strongly as the intact protein. In other RNA binding proteins with ARM motifs, residues outside the ARM also contribute to binding. Other families of RNA binding proteins with different binding motifs are described by Burd and Dreyfuss, supra.

2. Screening Methods

The invention provides methods of screening for RNA binding proteins that have desirable binding characteristics to selected RNA sequences. The methods can be used to isolate variants of known RNA binding proteins having altered (usually strengthened) binding characteristics. The methods are also useful for isolating hitherto unknown RNA binding proteins to any RNA sequence of interest. The unknown RNA binding proteins may be natural proteins encoded by cDNA or genomic libraries or synthetic peptides selected from a random combinatorial library. The methods can also be applied to screening a library of RNA recognition sequences to an RNA binding protein of interest.

There are two components of the screening system. The first component is a library encoding fusion proteins, each of which has at least two moieties. The first moiety is a peptide to be screened which varies between library members. The second moiety is a transcriptional inducer, which is the same in different library members. The transcriptional inducer is a peptide capable of inducing transcription from a promoter by binding to an RNA or DNA site proximal to the promoter. Binding brings the transcriptional-inducing domain of the fusion protein into proximity with the promoter and polymerase bound thereto thereby stimulating expression of a gene linked to the promoter. Usually, the natural RNA binding domain of a transcriptional inducer is deleted from fusion proteins, since its function is effectively replaced by the peptides being screened.

In some arrangements, the fusion proteins further comprise a linker or spacer polypeptide. The linker is usually be inserted between the peptide being screened and the transcriptional inducer. A linker (or spacer) refers to a molecule or group of molecules that connects two molecules or two parts of a single molecule. A linker serves to place the two molecules in a preferred configuration, e.g., so that each domain is functional without steric hindrance from the other. The spacer can be as short as one residue or as many as five to ten to up to about 100 residues. The spacer residues may be somewhat flexible, comprising polyglycine, or $(Gly_3Ser)_4$ for example. Alternatively, rigid spacers can be formed predominantly from Pro and Gly residues. Hydrophilic spacers, made up of charged and/or uncharged hydrophilic amino acids (e.g., Thr, His, Asn, Gln, Arg, Glu, Asp, Met, Lys, etc.), or hydrophobic spacers made up of hydrophobic amino acids (e.g., Phe, Leu, Ile, Gly, Val, Ala) can be used to present the RNA binding site with a variety of local environments.

The second component of the reporter system is a reporter construct. The reporter construct encodes a reporter gene (such as the GFP gene, β-galactosidase or chloramphenicol acetyl transferase) operably linked to a promoter and an RNA binding site. The choice of the promoter depends on the transcriptional inducer; that is transcription from the promoter should be capable of being stimulated by the transcriptional inducer. The RNA binding site can be the natural site recognized by a natural RNA binding domain of the transcriptional inducer or can be a heterologous site. If the latter, the site can be an RNA site for a known RNA binding protein, or an RNA site for which no known RNA binding protein is known but novel RNA binding peptides are sought. The RNA binding site is usually positioned between the promoter and the reporter coding sequence.

Both library members and the reporter construct are introduced into eucaryotic cells for the screen. The library members and reporter construct can be introduced concurrently or sequentially. Introduction of library members and/or reporter construct can be effected by the protoplast fusion method described above.

The screen works as follows. Most of the eucaryotic cells receive a nucleic acid library member encoding a fusion protein in which the peptide moiety lacks specific affinity for the RNA binding site on the construct or a transcript thereof. In these cells, the transcriptional inducer moiety is not brought into proximity with the promoter on the reporter construct and the reporter enzyme is expressed at basal levels. In one or a few eucaryotic cells, the cell receives a nucleic acid fragment encoding a fusion protein in which the peptide moiety has specific affinity for the RNA binding site in the reporter construct or a transcript thereof. In such a cell, the fusion protein binds to the RNA binding site on the construct or a transcript thereof via the peptide moiety, bringing the transcriptional inducer in proximity with the promoter on the reporter construct. The transcriptional inducer thereby stimulates expression of the reporter gene from the promoter. If the reporter gene is GFP, cells showing increased expression of the reporter can readily be identified by FACS sorting. The FACS method can screen large numbers of cells in liquid culture. A FACS machine can be programmed to isolate a fractionate of cells whose fluorescence exceeds a desired limit.

A preferred transcriptional inducer is HIV-1 TAT. Tat is a potent activator of HIV-1 gene transcription and is essential for viral replication. Tat activates transcription by enhancing the processivity of RNA polymerase II transcription complexes initiated at the HIV-1 LTR (Kao et al., 1987; Feinberg et al., 1991[Marciniak et al., 1991; Kato et al., 1992; Laspia et al., 1993), possibly by recruiting or enhancing the activity of cellular kinases that phosphorylate the CTD of RNA pol II, thereby creating elongation-competent polymerases (Parad et al., 1996; Yang et al., 1996; Zhou et al., 1996). To function, Tat must bind to TAR, an RNA hairpin located at the 5' end of nascent transcripts (Rosen et al., 1985; Roy et al., 1990). Tat contains a functionally defined activation domain (amino acids 1–48) and an arginine-rich RNA-binding domain (amino acids 49–57) that also functions as a nuclear localization signal (Dang et al., 1989; Hauber et al., 1989; Ruben et al., 1989). The activation and RNA-binding domains are modular and separable. Tat can activate transcription when bound to the nascent transcript through heterologous RNA-protein interactions (Selby et al., 1990; Southgate et al., 1990) or even when bound to DNA (Southgate et al., 1991). Thus, by assembling a reporter construct in which TAR is replaced with a "bait" RNA, it is possible to screen a library of fusion proteins comprising peptides linked to a Tat polypeptide containing at least the activation domain of Tat. For example, the bait RNA can be HIV RRE with a view to identifying peptides that antagonize binding of REV to HIV RRE and thereby abort the HIV infective cycle.

An analogous screen can be used to isolate RNA sequences that have specific binding affinity for a selected peptide. In this situation, a nucleic acid library is designed containing variants of a first construct. In each member of the library, the first construct contains a reporter coding sequence in operable linkage with a promoter, as described before. Between the coding sequence and promoter, there is a segment encoding potential RNA binding sequences that varies between members of the library. A second construct encodes a fusion protein comprising a transcriptional inducing domain linked to a selected peptide for which RNA binding sites are to be identified.

The library members are introduced into eucaryotic cells via protoplast fusion with primary cells, as described before. Preferably, the library members are transcribed in the primary cells so that transcripts of the first construct differing in the potential RNA binding site region are introduced into the eucaryotic cells together with the corresponding first constructs. The second construct can be transferred to eucaryotic cells from the primary cells concurrently with the library members. Preferably, the second construct is also expressed in the procaryotic cells so multiple copies of fusion protein are transferred to the eucaryotic cells. Alternatively, the library members and second construct can be introduced into eucaryotic cells sequentially.

The screen works in much the same manner as described above. That is, in eucaryotic cells having received a library members with an RNA binding site with specific affinity for the peptide moiety of the fusion protein, the fusion protein binds to the library member or a transcript thereof, inducing expression of the reporter gene in excess of basal levels. In cells having received a library member lacking an RNA binding site with specific affinity for the peptide moiety, the fusion protein does not bind to the library member or its transcript and the reporter is expressed at only basal levels.

RNA binding polypeptides isolated by the methods described above have a variety of uses. In one application, RNA binding polypeptides are used in therapeutic methods to block the life-cycle of pathogenic microorganisms, including viruses, such as HIV, and bacteria. Some synthetic RNA binding polypeptides are used as antagonists of a naturally occurring RNA binding protein. A synthetic polypeptide occupies the target site in competition with the natural protein or RNA without fulfilling the physiological role of the natural protein. The synthetic polypeptide thereby antagonizes the natural protein and aborts the life-cycle of a pathogenic microorganism. In such methods, the synthetic RNA binding polypeptide preferably has a higher binding affinity than the natural protein, and lacks functional domains (other than the binding domain) present in the natural protein. Other RNA binding polypeptides bind unique sequences on the pathogen's mRNA for which there may be no naturally occurring RNA binding protein. These polypeptide interfere with replication or translation of the pathogenic microorganism. For example, the RNA binding protein can occlude the Shine-Delgarno sequence or initiation codon of a bacterial mRNA thereby preventing translation. RNA binding sites recovered by the claimed methods can be used in an analogous manner to antagonize the binding of natural RNA sequences. In mammalian diseases resulting from impairment or loss of a natural RNA binding protein, treatment with an exogenous RNA binding protein or an analog that substitutes for, or agonizes a natural protein serves to ameliorate the disease. Some of these synthetic polypeptides possess both an RNA binding protein and a functional domain also present in the naturally occurring protein.

VIII. Analogs

Binding-peptides isolated by the methods can serve as lead compounds for the development of derivative compounds. The derivative compounds can include chemical modifications of amino acids or replace amino acids with chemical structures. The analogs should have a stabilized electronic configuration and molecular conformation that allows key functional groups to be presented to the binding site in substantially the same way as the lead peptide. In particular, the non-peptidic compounds have spatial electronic properties which are comparable to the polypeptide binding region, but are typically much smaller molecules than the polypeptides, frequently having a molecular weight below about 2 kD and preferably below about 1 kD.

Identification of such non-peptidic compounds can be performed through use of techniques known to those working in the area of drug design. Such techniques include, but are not limited to, self-consistent field (SCF) analysis, configuration interaction (CI) analysis, and normal mode dynamics analysis. Computer programs for implementing these techniques are readily available. See Rein et al., *Computer-Assisted Modeling of Receptor-Ligand Interactions* (Alan Liss, New York, 1989).

IX. Diagnostic and Therapeutic Compositions

Peptides and other compounds identified by the above methods or their analogs are formulated for therapeutic use as pharmaceutical compositions. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The polypeptides and compounds isolated by the methods are also useful in diagnostic methods. For example, an RNA binding polypeptide with a specific affinity for an RNA sequence encoded by a pathogenic microorganism can be used to detect the microorganism. In one assay format, the polypeptide is immobilized to a support, optionally via a linker, and a sample, which may or may not contain RNA from the microorganism, is contacted with the support. Bindings of the RNA from the microorganism to the support can be detected by competition with binding of a labelled synthetic RNA recognition sequence to the immobilized RNA binding polypeptide. RNA binding polypeptides are also useful in controlling the growth of cells in culture.

The following examples are provided to illustrate but not to limit the invention.

EXAMPLES

1. Experimental Procedures a. Plasmid Construction

The HIV-1 LTR-GFP reporter plasmid (containing wild-type TAR) was constructed by inserting a gene encoding the Ala65 GFP mutant (containing a GCC alanine codon in place of the TCT serine codon) between the Hind III and Xho I sites in pCDNA3 (Invitrogen), and by replacing the CMV promoter of pCDNA3 with the HIV-1 LTR from pHIV-CAT (Rosen et al., 1985). BUV TAR and RRE IIB GFP reporters were constructed by replacing the HIV-1 LTR-TAR region with corresponding regions from BIV TAR and RRE IIB CAT reporters (Tan et al., 1993; Chen and Frankel, 1994). The U1 GFP reporter was constructed by replacing the top part of TAR (+20 to +40) with an oligonucleotide containing the 22-nucleotide U1 snRNA hairpin II (Oubridge et al., 1994). Tat-Rev$_{14}$, Tat-Arg$_{14}$, and selected Tat-peptide hybrids were constructed by cloning oligonucleotide cassettes encoding each peptide plus four alanines at the N-terminus and four alanines and an arginine at the C-terminus after amino acid 49 of Tat (using an Eag I site at the end of the activation domain) in vectors derived from pSV2tat72 (Frankel and Pabo, 1988). The Tat-U1A fusion was constructed by fusing oligonucleotide cassettes encoding three glycines followed by residues 2–102 of U1A to Tat$_{1-72}$ (kindly provided by S. Landt). All constructs were confirmed by dideoxynucleotide sequencing.

b. Stable Cell Lines

HeLa cell lines containing stably integrated HIV-1 LTR-GFP reporters were selected using neomycin (G418). Cells were transfected by lipofection with plasmids encoding each reporter and were grown in Dulbecco's modified Eagle medium (DMEM) containing 10% fetal bovine serum and 1 mg/ml neomycin. The medium was changed every four days. Following serial dilution in 96-well plates and 3–4 weeks of growth, single colonies were chosen and tested for GFP expression after transfecting with plasmids expressing the corresponding Tat fusion. Clones with low backgrounds in the absence of the Tat fusion and bright fluorescence in the presence of the fusion, as judged by fluorescence microscopy, were selected for expansion.

c. Protoplast Preparation and Fusion

Single DH-5α colonies containing appropriate plasmids were inoculated into 5 ml LB medium containing 100 μg/ml ampicillin, and cells were grown overnight at 37° C. with moderate shaking. Overnight cultures (0.5 ml) were added to 50 ml LB containing ampicillin, cells were grown at 37° C. to $A_{600}$=0.7–0.8, chloramphenicol was added to 250 μg/ml, and plasmids were amplified by growing for an additional 16 hr at 37° C. Cells were centrifuged at 2000×g for 10 min at 40° C., cell pellets were resuspended 10 ml 50 mM Tris-Cl (pH 8.0) and centrifuged again at 2000×g for 10 min at 4° C. Protoplasts were prepared using a previously described protocol (Sandri-Goldin et al., 1981) as follows: A Cells were resuspended in 2.5 ml chilled 20% sucrose in 50 mM Tris-Cl (ph 8.0), 0.5 ml 5 mg/ml lysozyme (freshly prepared in 0.25 M Tris-Cl, pH 8.0) was added, and cells were incubated on ice for 5 min. One ml 0.25 M EDTA (pH 8.0) was added and cells were incubated on ice for an additional 5 min. One ml 50 mM Tris-Cl (pH 8.0) was added slowly and the mixture was incubated at 37° C. until all bacteria were converted to protoplasts, as monitored by phase-contrast microscopy (bacteria are rod-shaped whereas protoplasts are round). For DH-5α cells, conversion to protoplasts takes about 15 min. Protoplasts were then carefully and slowly diluted with 20 ml room temperature serum-free DMEM containing 10% sucrose and 10 mM $MgCl_2$ and suspensions were kept at room temperature for 15 min. These preparations contain ~$1.5 \times 10^9$ protoplasts per ml and are ready for fusion.

Prior to fusion, HeLa cells were split into 6-well plates and grown for 24 hr to ~70% confluence. Medium was removed and cells were washed with 4 ml serum-free DMEM per well. Four ml of protoplast suspensions (~$6 \times 10^9$ protoplasts; protoplasts should be >1000-fold excess over cells) was added and plates were configured at 1650×g for 10 min at 25° C. Supernatants were removed carefully by suction. Two ml pre-warmed 50% (v/v) PEG1000 or 50% (W/V) peg1500 was added at room temperature, left for 2 min. And removed by suction. Cells were washed three times using 2 ml serum-free DMEM, and 4 ml DMEM containing 10% fetal bovine serum, penicillin, streptomycin, and kanamycin was added. Medium was changed after 24 hr, and cells were grown for an additional 24 hr before examining fluorescence.

d. FACS

Protoplast-fused or transfected cells were harvested by trypsinization after 48 hours and were resuspended at a concentration of $10^6$ cells/ml in DMEM containing 10% cell dissociation buffer (GIBCO-BRL), 0.3% fetal bovine serum, and 1 μg/ml propidium iodide. Samples were analyzed or sorted by FACS using an argon laser to excite cells at 488 nm and a 530±30 nm band pass filter to detect GFP emission. For FACS scans, 10,000 cells were typically analyzed using a FACScan flow cytometer (Becton Dickinson, San Jose, Calif.). For FACS sorting, 2000–3000 cells were sorted per second, propidium iodide-staining cells were removed electronically, and cells of interest were collected into Eppendorf tubes containing 0.5 ml DMEM. Sorting was performed using a Howard Hughes Medical Institute (UCSF) FACSTAR+ cell sorter (Becton Dickinson). FACS data were analyzed using CellQuest software.

e. Plasmid Recovery from FACS-Sorted Cells

FACS-sorted cells were mixed with 20,000 HeLa cells and centrifuged at 15000×g for 5 min at 4° C. Cell pellets were resuspended in 10 μl TE buffer (pH 8.0) containing 0.2 mg/ml tRNA, cells were lysed by adding 20 μl 1% SDS, 0.2N NaOH, and suspensions were incubated on ice for 5 min. Fifteen μl 3M NaOAc (pH 4.8) was added, mixtures were incubated on ice for 10 min and then centrifuged at 15000 ×g for 5 min at 4° C. Supernatants were transferred to fresh tubes and extracted with an equal volume of phenol:chloroform (1:1). Plasmid DNAs were precipitated by adding 1 μl/ml glycogen (Sigma), 0.1 vol 3M NaOAc (pH 4.8), and 3 vol ethanol (–20° C.), incubating on dry ice for 1 hr, and centrifuging at 15000×g for 30 min. Pellets were washed with 70% ethanol (–20° C.), air dried, and dissolved in 1 μl distilled water.

f. Preparation of Electrocompetent Cells and Electroporation

Single DH-5α colonies were inoculated into 5 ml LB, cells were grown at 37° C. with moderate shaking overnight, and 2.5 ml was used to inoculate 500 ml LB cultures. Cells were grown at 37° C. with shaking to $A_{600}$=0.5–0.6 and then chilled in ice water for 15 min. Cells should be kept at 0° C. for all subsequent steps. Cells were centrifuged in a swinging bucket rotor at 4000×g for 20 min, pellets were resuspended in 500 ml ice-cold 1 mM HEPES (pH 7.0), centrifuged at 4000×g for 20 min, and the HEPES wash was repeated. Cells were then resuspended in 250 ml ice cold water, centrifuged at 4000×g for 20 min, and the water wash was repeated. These four washing steps are critical for obtaining highly electrocompetent cells and must be performed carefully to avoid loose cell pellets. Cells were then resuspended in 100 ml ice-cold glycerol, centrifuged at 4000×g for 10 min, and resuspended in one half the cell volume of ice-cold glycerol. Cell densities are typically ~$3 \times 10^{11}$/ml. If frozen electrocompetent cells are desired, 100 μl aliquots can be frozen on dry ice and stored at –80° C. Frozen cells generally give 2–3 fold fewer transformants than fresh cells.

For electroporation, recovered plasmid DNAs (1 μl) were added to 50 μl electrocompetent cells on ice, and cells were electroporated at 1.8 KV, 25 μF, and 200 ohms using 1 mm cuvettes (BioRad). One ml room temperature SOC medium was immediately added to the cuvettes, cells were transferred to culture tubes, incubated with moderate shaking for 60 min at 37° C., and spread on DLB plates containing 100 μg/ml ampicillin. Using small amounts of supercoiled pUC19 plasmid DNA (0.1–10 pg), efficiencies of ~$1.5 \times 10^{11}$ colonies/μg DNA were typically obtained.

g. Combinatorial Peptide Library Design and Screening

A degenerate oligonucleotide (5'-ATCTCTTACGGCCGTGCCGCT GCAGCCXXYA-GAXXYXXYAGGCGAXXYAGGAGACGGC-GACGTCGCAGAGCTGCCGCCGCAAG ATGACTCGAGACTAGTGGA-3' (SEQ ID NO:23), where X is A:G:C mixture at a 1:1:1 ratio and Y is a G:T mixture at a 1:1 ratio) was synthesized encoding the arginine-rich peptide library. A primer (5'-TCCACTAGTCTCGAG-3' (SEQ ID NO:24)) was annealed to the degenerate oligonucleotide, and double-stranded DNA was synthesized using Sequenase 2.0 (USB). The double-stranded product (~0.1 μg) was digested with Eag I and Xho I and ligated into 5 μg Eag I-Xho I-digested pSV2rat72 to generate fusions to amino acid 49 of Tat. The encoded peptides contain four randomized positions within a stretch of fourteen arginines, AAAAXRXXRRXRRRRRRRAAAAR (SEQ ID NO:3), where X represents any of twelve amino acids in the bold box in FIG. 6A. Ligation products were phenol extracted, ethanol precipitated, and ~0.2 μg was electroporated into DH-5α cells. Immediately following electroporation, $7 \times 10^7$ individual clones were obtained, 700-fold larger than the sequence complexity of the library. Cells were amplified to $2 \times 10^9$ by growing in LB for 3 hr, centrifuged, resuspended in 5 ml glycerol stock buffer (50% LB, 32.5% glycerol, 50 mM MgSO$_4$, 12.5 mM Tris-Cl, pH 8.0), and stored at −80° C. in 1 ml aliquots. Sequences of 18 individual colonies from the amplified cells indicated no sequence bias.

One ml of the library stock (~10$^8$ cells) was inoculated into 100 ml LB/ampicillin, and cells were grown at 37° C. to A$_{600}$=0.7–0.8. Parallel 50 ml cultures containing Tat-Rev$_{14}$ and Tat-Arg$_{14}$ plasmids were grown. Chloramphenicol was added to 250 μg/ml and cells were grown for an additional 16 hr. Protoplasts were prepared and fused to HeLa cells containing a stably integrated HIV-1 LTR RRE IIB-GFP reporter. After 48 hours, 10,000 positive control cells (Tat-Rev$_{14}$) and 10,000 negative control cells (Tat-Arg$_{14}$) were analyzed by FACS to estimate fusion efficiency and to establish the sorting window. Library-fused cells (Π10$^7$) were sorted by FACS and positive cells were collected. Plasmids were recovered by alkaline-lysis phenol-extraction and electroporated into DH-5α cells. Resulting colonies were harvested from 5 plates using 5 ml LB per plate, cells were centrifuged, resuspended in 4 ml glycerol stock buffer, and 2 ml was used to inoculate 100 ml LB/ampicillin to prepare protoplasts for the next round of selection. The cycle was repeated for three rounds, until the fraction of GFP-positive cells was similar to that of the positive control.

h. CAT Assays

Levels of activation by the Tat fusion proteins were assessed by cotransfecting 50 ng of an HIV-1 LTR RRE IIB-CAT reporter plasmid (Tan, R. et al. (1993). Rna recognition by an isolated alpha helix, *Cell* 73:1031–1040) and 0.2–25 ng Tat expression plasmids into HeLa cells using lipofectin. Total plasmid DNA was adjusted to 1 μg with pUC19. CAT activities were assayed after 48 hr using an appropriate amount of cell extract as described (Calnan, B. J. et al. (1991). Analysis of arginine-rich peptides from the HIV Tat protein reveals unusual features of RNA-protein recognition. *Genes Dev* 5:201–10), and activities 2. Results The basic protocol for screening RNA-binding libraries is outlined in FIG. 1. The Tat activation domain, or in some cases full-length Tat, was fused to a library and an HIV-LTR GFP reporter was constructed in which an RNA site of interest replaced the TAR site. The library was delivered into reporter-containing HeLa cells by protoplast fusion under conditions in which approximately one bacterium fused to one cell. After two days, HeLa cells expressing high levels of GFP were sorted by FACS, and plasmids were extracted and electroporated into bacteria. The procedure was repeated using protoplasts from the enriched population until most cells expressed GFP, and resulting plasmids were sequenced.

Figures 1, 2:
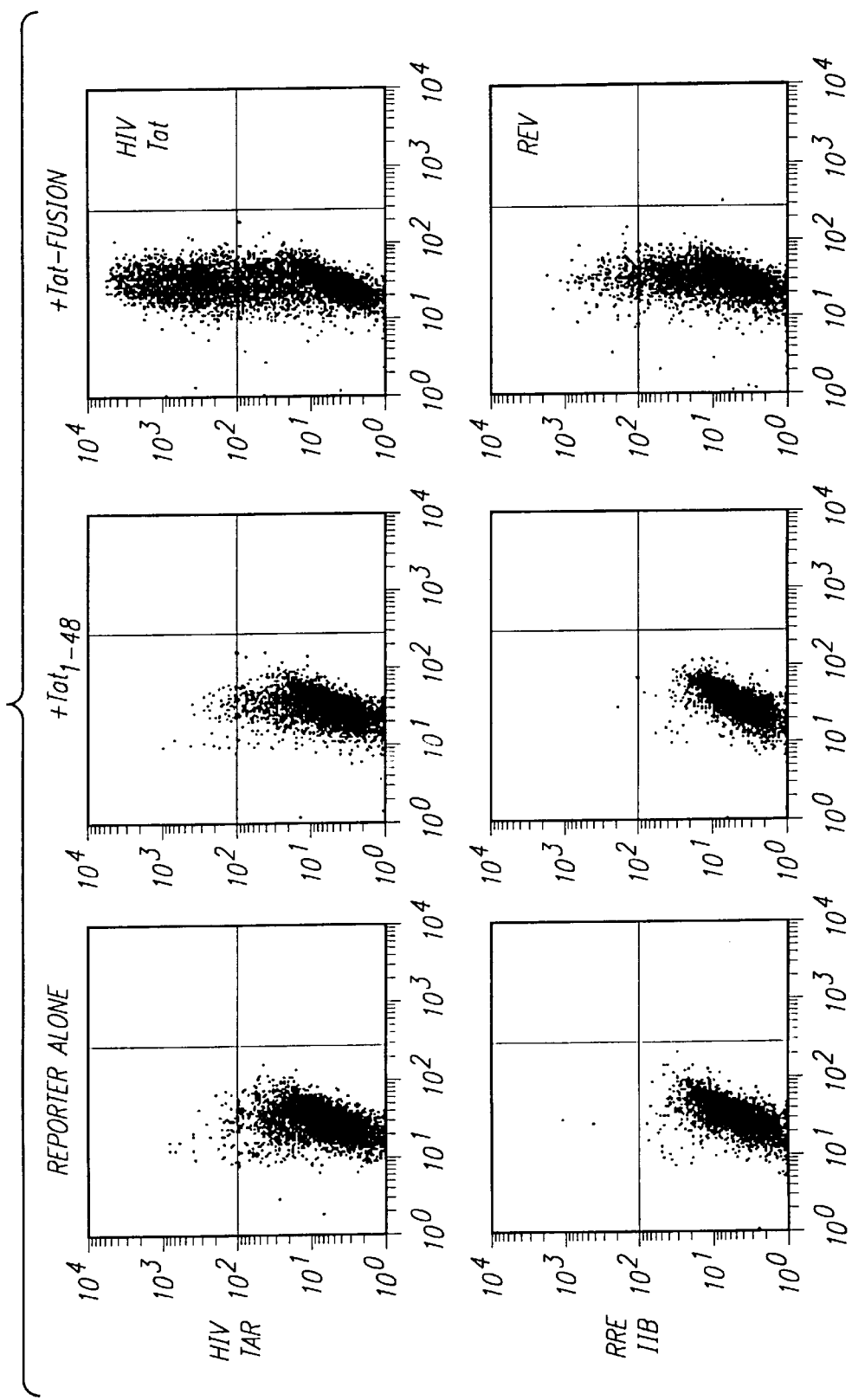
FIG. 2. Activation of GFP expression by Tat fusion proteins and corresponding RNA reporters. Cells were lipofected with HIV TAR, RRE IIB, BIV TAR, or U1 hpII GFP reporters alone (left column), along with Tat1-48 or Tat1-72 (middle column), or along with full-length HIV Tat or Tat fusions to a Rev peptide, BIV Tat peptide, or U1A RNA-binding domain, respectively (left column). Rev and BIV Tat peptides were fused to Tat1-48 whereas the U1A domain was fused to Tat1-72 to ensure nuclear localization. Plots show relative GFP fluorescence on the y-axis and relative side scatter (a measure of cell granularity) on the x-axis for 10,000 cells.
Figure 2:
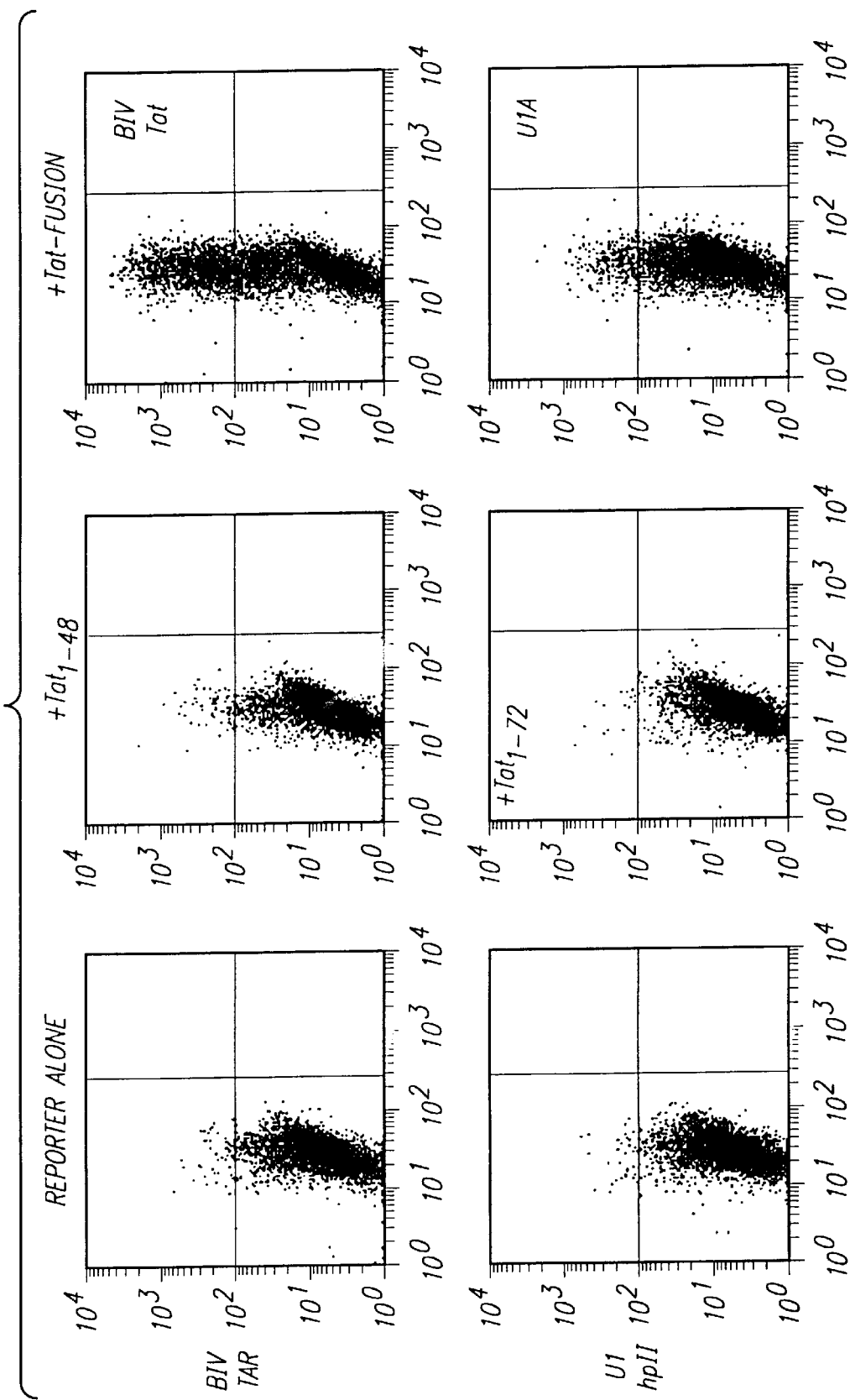

To test whether the Tat-GFP reporter system could be used to monitor specific RNA-protein interactions, we first constructed a set of reporters containing HIV TAR, RRE IIB (the high-affinity Rev binding site), bovine immunodeficiency virus (BIV) TAR, and U1 snRNA hairpin II (the U1A protein binding site), and a set of Tat fusions containing the RNA-binding domains from HIV Tat, Rev, BIV Tat, and the U1A protein (Calnan et al., 1991; tan et al., 1993; Chen et al., Frankel, 1994; Oubridge et al., 1994; Harada et al., 1996). GFP reporters were transfected into HeLa cells by lipofection either alone or with Tat fusions, and expression was monitored by fluorescence microscopy and FACS. GFP expression was observed only with the cognate partners. The activation domain of Tat alone (Tat1-48) did not activate through HIV TAR, RRE, or BIV TAR reporters, and full-length Tat (Tat1-72) did not activate through U1 hpII (FIG. 2). U1A was fused to Tat1-72 to ensure nuclear localization (the arginine-rich domain of Tat functions as an NLS) whereas the other RNA-binding domains were fused to Tat1-48 because they provide their own NLS. When reporters were cotransfected with the corresponding Tat fusion proteins, GFP expression increased ~10–100-fold (FIG. 2). No activation was observed through noncognate RNAs, as monitored either by FACS or fluorescence microscopy, indicating that the Tat-GFP reporter system accurately reflects specific RNA-protein interactions. The Tat-U1A fusion, which contains the arginine-rich RNA-binding domain of Tat, also functioned through HIV TAR.

We examined the properties of GFP variants having different fluorescence intensities in stable reporter-containing cell lines and by transient transfection. The signals obtained with Ala65 and Thr65 mutants (Cubitt et al., 1995; Cormack et al;, 1996) were significantly higher than wild-type GFP, and the signal from a GFP gene in which codons were optimized for mammalian expression (EGFP; Clontech; Haas et al., 1996) was even higher. However, because EGFP produced substantial fluorescence even in the absence of Tat, we chose to use the Ala65 mutant, which gives slightly brighter fluorescence than Thr65, for subsequent experiments.

a. Introduction of Plasmids by Protoplast Fusion

To facilitate screening of relatively large libraries (~10$^6$–10$^7$ members), an approach was designed to deliver many copies of a single library member into each recipient cell. In principle, clonal or near-clonal delivery allows relatively weak binders to produce detectable GFP signals and reduces the background from other members of the library, while delivery of a sufficient number of copies might allow plasmid recovery without additional amplification. Unlike bacteria or yeast where plasmid segregation results in clonal colonies, transfection of mammalian cells is believed to involve the uptake of a large population of plasmids [xx]. We reasoned that "pre-packaging" the plasmid DNA might allow delivery of a more homogeneous population, and that bacterial protoplast fusion (Scaffner, 1980; Seed et al., 1987 might provide a good vehicle to deliver many copies of a single plasmid. With chloramphenicol amplification, as many as 3000 copies of a ColE1 origin-containing plasmid can be expressed in *E. coli* (Clewell, 1972).

Figure 3A:
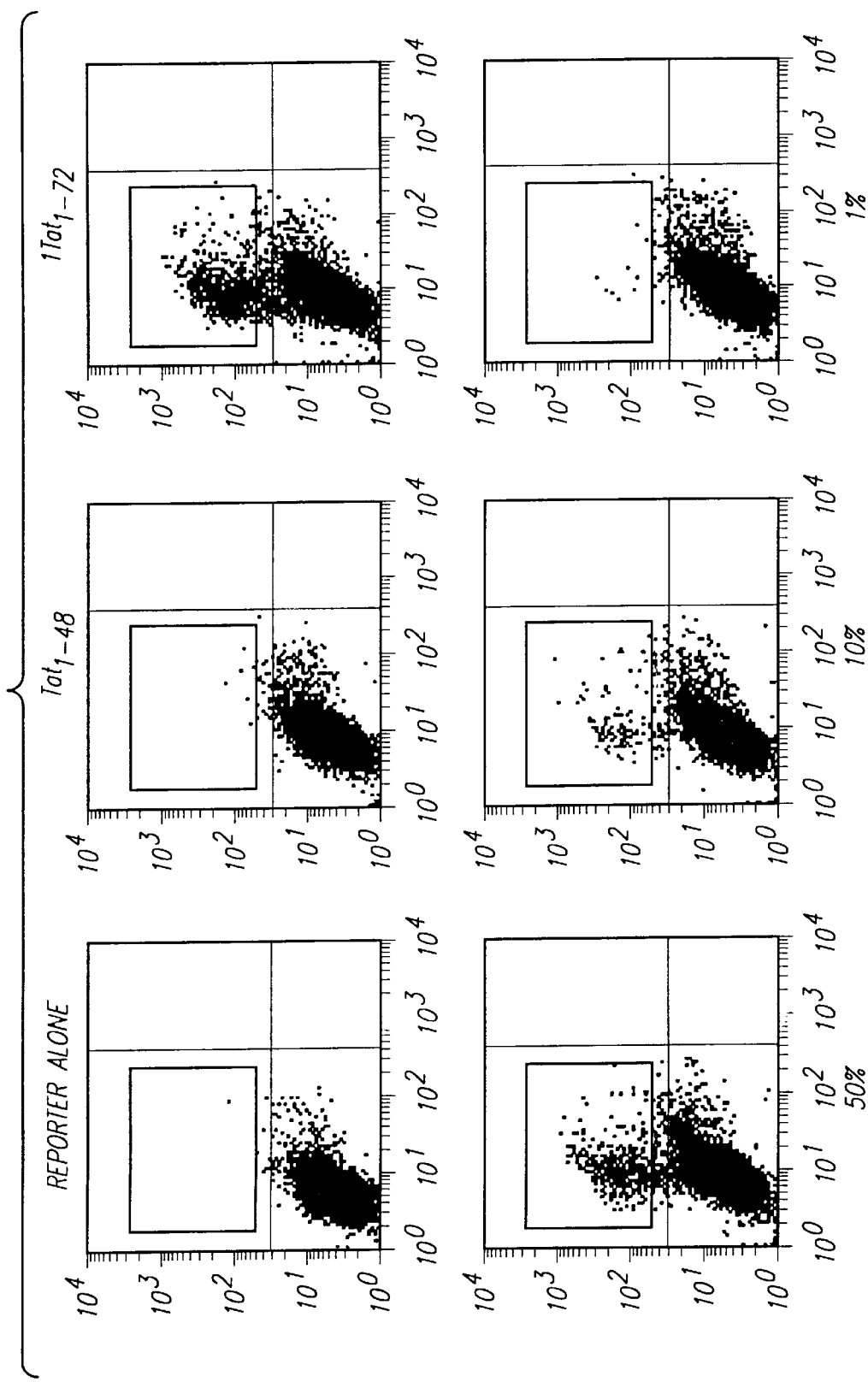
FIG. 3. Delivering plasmids by protoplast fusion activates GFP expression. (A) FACS analysis of cells containing a stably-integrated HIV-1 LTR-GFP reporter (reporter alone) or reporter cells fused with protoplasts containing pSV2Tat1-48 or pSV2Tat1-72 plasmids, or fused with protoplast mixtures containing pSV2Tat1-72 and pSV2Tat1-48 in 1:1 (50%), 1:10 (10%), or 1:100 (1%) ratios. Percentages refer to the proportion of pSV2Tat1-72 in the mixture. (B) Plot of the percentage of GFP-expressing cells as a function of the proportion of pSV2Tat1-72 in the mixture, from (A). Based on the percentage of positive cells obtained with pSV2Tat1-72 alone, about 10% of cells fused in this experiment.
Figure 3B:
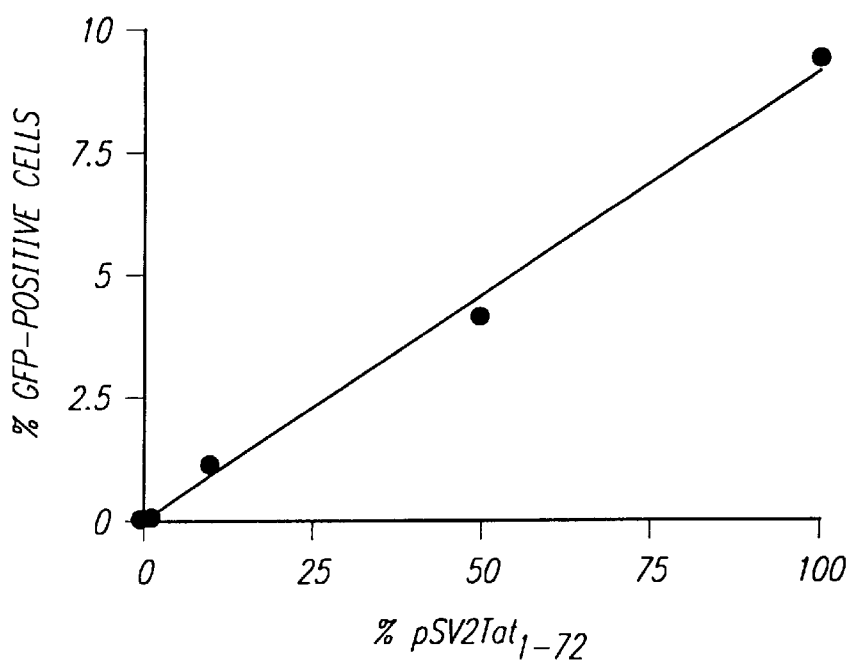

To test whether protoplast fusion would be suitable in our system, we first fused protoplasts containing amplified pSV2Tat1-72 or pSV2Tat1-48 plasmids into HeLa cells containing a stably integrated HIV-1 LTR-TAR-GFP reporter. Approximately 10% of cells fused with pSV2Tat1-72 displayed high GFP fluorescence as monitored by microscopy and FACS analysis(FIG. 3A) whereas fusion to pSV2Tat1-48 produced virtually no signal. Remarkably, diluting pSV2Tat1-72 protoplasts with increasing amounts of inactive pSV2Tat1-48 protoplasts resulted in a proportional decrease in the number of GFP-expressing cells, but not a proportional decrease in fluorescence intensity (FIGS. 3A and 3B). This result suggests that, statistically, few protoplasts (perhaps as few one) delivered their contents into each HeLa cell, even at relatively high (10–20%) fusion efficiencies. In contrast, the same ratio of plasmids delivered by lipofection resulted in a proportional decrease in fluorescence intensity and was too low to be detected with 1% pSV2Tat1-72, as expected if cells were randomly sampling the distribution of plasmids in the transfection mixture. Thus, it appears that protoplast fusion results in near-clonal delivery of plasmids into HeLa cells even though efficient fusion requires a large excess (>1000) of protoplasts to cells (Rassoulzadegan et al., 1982) and many protoplasts bind to each cell as judged by light microscopy. Clonal delivery may arise because fusion is very inefficient or because delivery of so many plasmids saturates the cellular DNA entry system and preclude uptake of additional plasmids.

b. Recovery of Plasmids from FACS-sorted Cells

Figure 4:
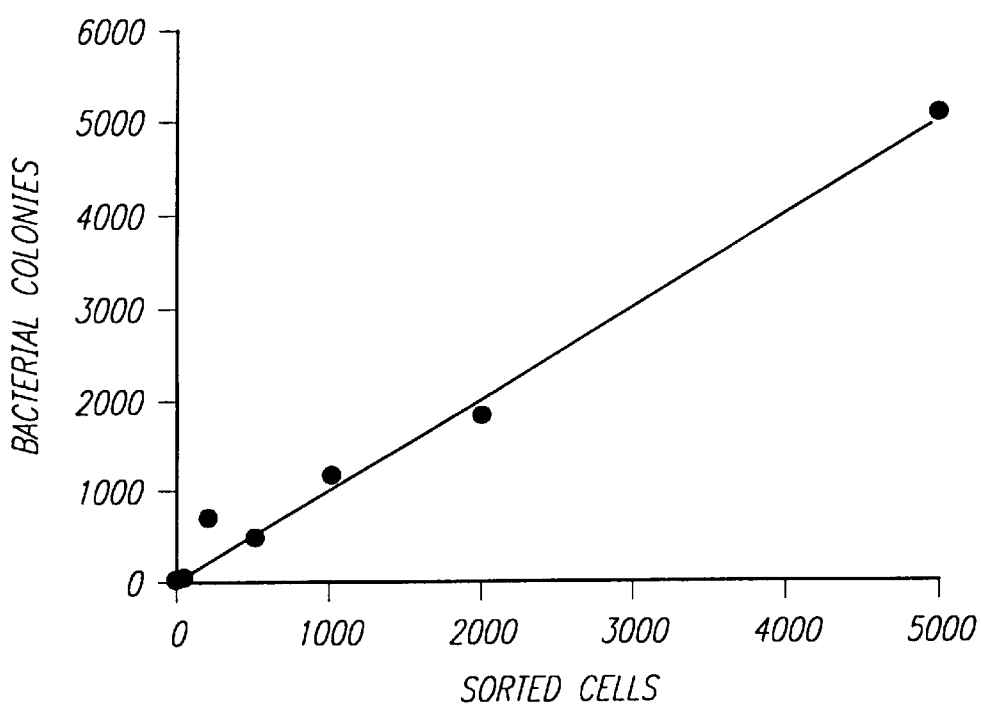
FIG. 4. Plasmid recovery from FACS-sorted GFP-positive cells. HIV-1 LTR-GFP reporter cells were fused with protoplasts expressing Tat1-72 and positive cells were sorted. Plasmids were extracted by alkaline-lysis and phenol-extraction from 50–5000 positive cells, with 20,000 HeLa cells added as carrier, and were electroporated into DH-5α cells. The number of colonies produced was plotted against the number of positive cells used for each plasmid preparation.

Though in principle protoplasts deliver many plasmids into a cell, it was unclear whether a substantial fraction of plasmid DNA would remain intact after the 48 hours required to express GFP and sort cells, and whether the few remaining plasmids could be efficiently recovered. Previous expression cloning strategies have relied on plasmid replication in recipient cells, most often using an SV40 origin and T-antigen-expressing cells (such as COS) to amplify plasmids episomally (Seed, 1995). Indeed, without amplification recovery was quite poor in our hands and required modification of the cell lysis procedure and preparation of highly electrocompetent cells (~$1.5 \times 10^{11}$ colonies/mg pUC19 with DH-5α cells) to achieve reasonable efficiencies. To test plasmid recovery from the small number of positive cells expected from a library screen, we fused pSV2Tat1-72 protoplasts into HeLa GFP reporter cells and collected positive cells by FACS sorting. Hirt supernatants (Hirt, 1967) prepared from ~50 cells typically yielded <0.1 colony per sorted cell. In contrast, an alkaline-lysis phenol-extraction protocol in which untransfected HeLa cells, tRNA, and glucose were added to reduce plasmid loss yielded ~1 colony per sorted cell (FIG. 4). Although more efficient recovery would help ensure that individual plasmids are not lost from the sorted population, it is possible to screen reasonably sized libraries (~$10^6$ members) using the current procedure and sorting multiple representatives of each positive cell (see Discussion).

c. Screening for Positive Clones in a Mock Library

Figure 6C:
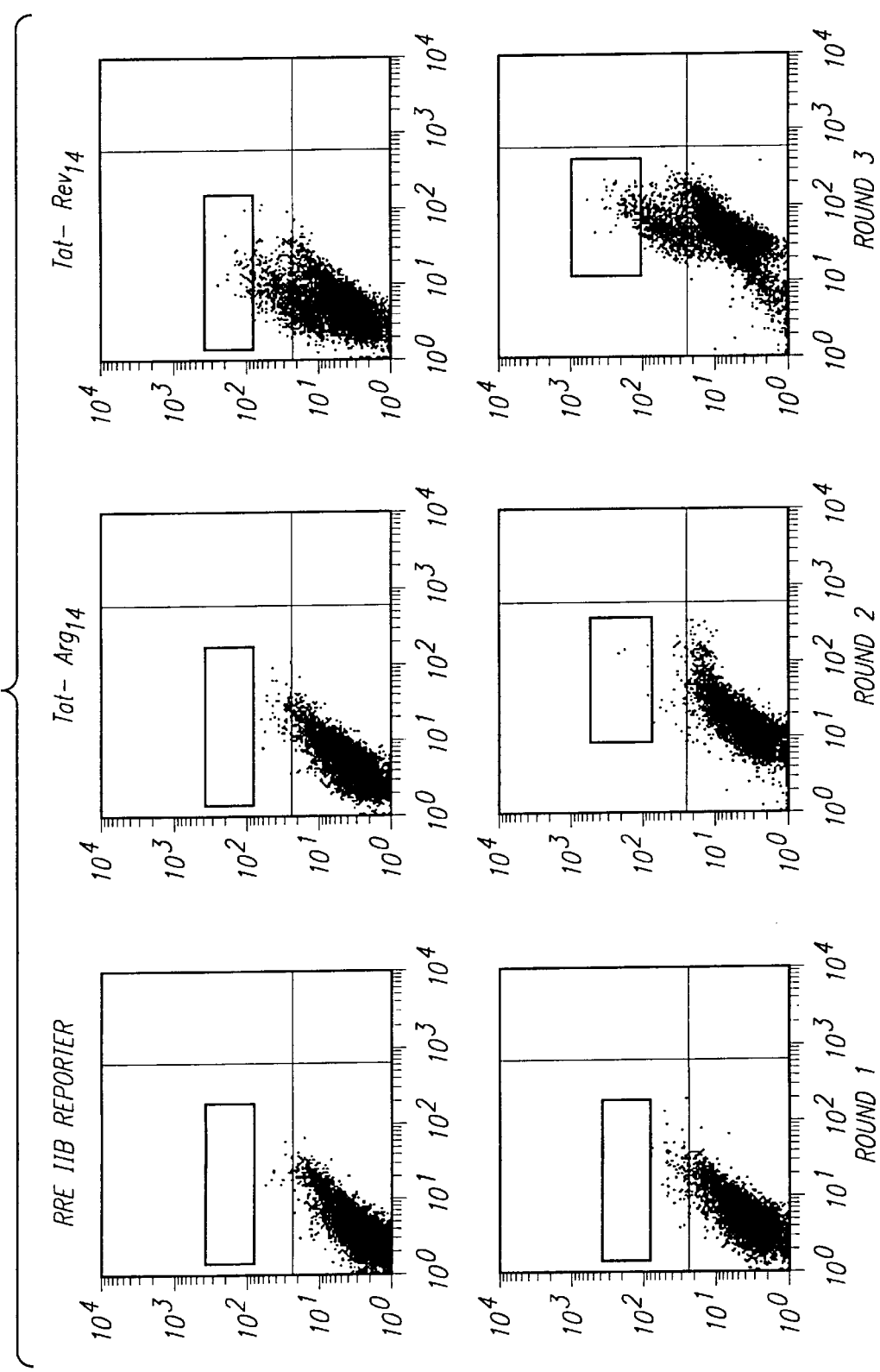
FIG. 6. Screening an arginine-rich combinatorial library for RRE binders. (A) The genetic code viewed from the perspective of arginine-rich peptides. Amino acids known to be important for specific RNA binding by HIV-1 Rev, HIV-1 Tat, BIV Tat, and λN peptides are indicated in bold (Harada et al., 1996). A restricted genetic code (bold box) encodes all charged and hydrophilic residues, glycine, alanine, and proline, and contains all six arginine codons. Combinations of these amino acids in an arginine-rich context are expected to encode a variety of helical and nonhelical RNA-binding peptides. (B) A 14-amino acid Rev peptide (Rev14 corresponds to residues 34–47 of Rev, with Trp45→Arg and Glu47→Arg substitutions, and specifically binds RRE IIB RNA) and 14 arginines were fused to the HIV-1 Tat activation domain (residues 1–49) in the context of surrounding alanines as shown. In the library (SEQ ID NO:3), 4 residues corresponding to non-arginine positions in Rev were randomized with the amino acids encoded by the bold box in (A) and are highlighted. Rev14 (SEQ ID NO:1) served as a positive control and Arg14 (SEQ ID NO:2) as a negative control. (C) FACS analysis of the reporter alone, cells fused to negative and positive control protoplasts used to set sorting windows (boxes), and library-containing protoplasts carried through three rounds of sorting, as described in FIG. 5 and in the text. Individual clones from Round 3 were tested for activity and positive clones were sequenced.

To mimic the situation encountered in a library screen, we next tested the ability to recover a small number of active plasmids from a large pool of inactive plasmids. Protoplasts containing pSV2Tat1-72 and pSV2Tat1-48 were mixed in a $1:10^5$ ratio and fused to HeLa GFP reporter cells. After 48 hours, $1.1 \times 10^7$ cells were sorted and 893 GFP-positive cells were collected (FIG. 5, Round 1). Plasmids were extracted, electroporated into DH-5α cells, and 1140 colonies were obtained. Twenty colonies were analyzed by PCR and all contained pSV2Tat1-48. In the second round, protoplasts were prepared from a mixture of the 1140 colonies, $3 \times 10^6$ cells were sorted, and 710 positive cells were collected (FIG. 5, Round 2). From these, 800 colonies were obtained, and of twenty analyzed by PCR, two contained pSV2Tat1-72 and the remainder contained pSV2Tat1-48. In the third round, $5 \times 10^5$ cells were sorted, 3000 positive cells were collected, and 890 colonies were obtained (for technical reasons, cells were sorted after 96 hours and plasmid recovery was reduced). Twelve of twenty colonies analyzed by PCR contained pSV2Tat1-72. Thus, positive clones were enriched from 1 in 105 to 60% after three rounds of screening. A similar level of enrichment was observed after three rounds of screening using protoplast fusion and a replicating vector in COS cells (Seed et al., 1987).

d. Identification of Tight RRE-binding Peptides from a Combinatorial Library Previous studies have shown that arginine-rich peptides can bind to RNA sites with high affinities and specificities using a variety of conformations for recognition (Calnan et al., 1991; Tan et al., 1993; Chen et al., 1995; Harada et al., 1996). For example, a Rev peptide binds to the RRE in an a-helical conformation whereas a BIV Tat peptide binds to BIVTAR as a β-hairpin (Puglisi et al., 1995; Ye et al., 1995; Battiste et al., 1996; Ye et al, 1996). In each case, few amino acids other than arginine provide specific contacts to the RNA (see FIG. 6A), leading to the hypotheses: 1) that specific RNA-binding peptides could have evolved relatively easily beginning with polyarginine and 2) that it might be possible to identify novel RNA-binding peptides from combinatorial libraries restricted to relatively few types of amino acids (Harada et al., 1996; Harada et al., Frankel, 1997). To further explore these hypotheses, we designed a combinatorial library in which four residues within a stretch of fourteen arginines were randomized using twelve hydrophilic or charged amino acids (FIGS. 6A and 6B). The randomized positions correspond to non-arginine residues in Rev (FIG. 6B), and the library contains $18^4$ (~$1 \times 10^5$) codon sequences encoding 124 (~$2.1 \times 10^4$) peptides. The library was fused to the Tat activation domain in the context of flanking alanines to help stabilize α-helical conformations (Tan et al., 1993; Tan et al., 1994), and the library was screened for tight RRE binders using a HeLa cell-line containing a stably integrated HIV-1 LTR-RRE IIB-GFP reporter. Protoplasts containing Tat-Rev14 and Tat-Arg14 were used as positive and negative controls (FIG. 6C), and the sorting window was set to identify fusion proteins with higher activities than Tat-Rev14, presumably reflecting tighter binding to the RRE IIB site. Three rounds of screening were performed; $7 \times 10^6$ cells were sorted in the first round and 800 positive cells were collected, and increasing numbers of strong GFP expressors were observed in the two subsequent rounds (FIG. 6C). Plasmids from 51 individual clones were tested for activation of the RREIIB-GFP reporter and 36 showed high level expression by fluorescence microscopy. Six unique sequences were found (FIG. 7), two containing glutamine at position 7 (clones 1 and 2) and four containing frame shifts near the C-terminus of the peptide that introduced a glutamine followed by additional basic residues (clones 4–6). An additional screen was performed in which the sorting window was set slightly lower, and 15 additional RRE binders were found, 12 containing at least one glutamine, predominantly at position 7 (FIG. 7).

Figure 8A:
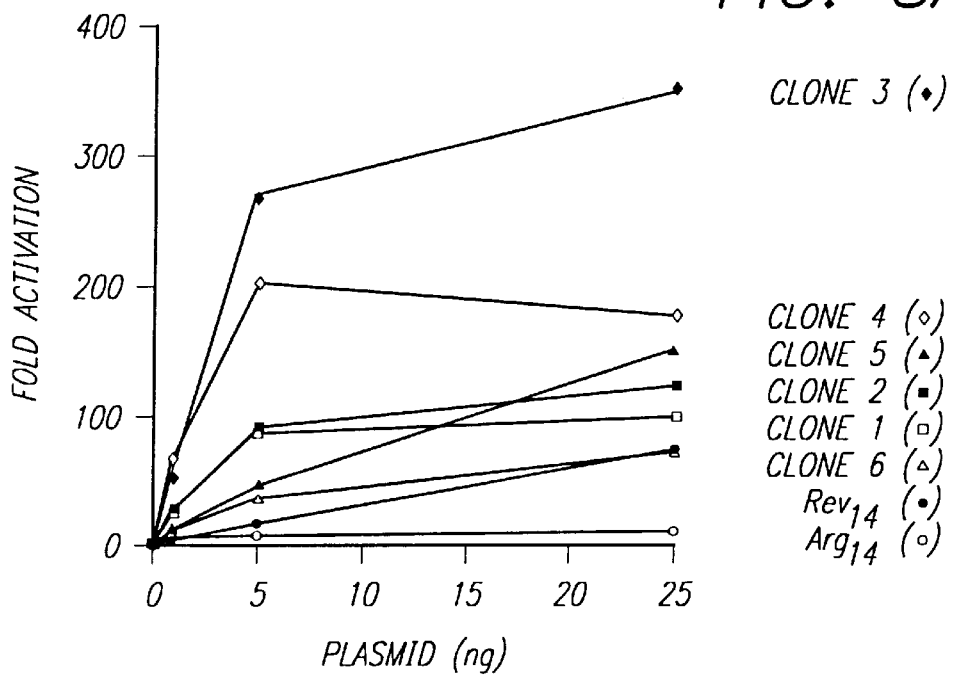
FIG. 8. Activities of Tat fusion proteins on an HIV-1 LTR RRE IIB-CAT reporter. (A) The Tat fusion plasmids shown (1, 5, and 25 ng) were cotransfected with the reporter (50 ng) and CAT activities were measured after 48 hr. Fold activation was calculated as the ratio of activities with and without the Tat-expression plasmids. (B) Activities of Tat fusions containing R6QR7, R6NR7, and the Rev14(N→Q) mutant, determined as in (A).

To more quantitatively assess RNA-binding activities and to compare the activities observed with the GFP reporter to a known reporter, we measured activities of the selected Tat fusions using an HIV-1 LTR RREIIB-CAT reporter which shows a tight correlation between in vivo activation and specific in vitro RNA-binding affinities (Tan et al., 1993; Tan et al., 1994; Symensma et al., 1996). All Tat fusions that activated GFP expression to high-levels (clones 1–6) also activated CAT expression to high levels, and the best fusions were 5–10-fold more active than Tat-Rev14 (FIG. 8A). Binding to the RRE IIB site is specific as judged by the inability of the fusions to activate through an RNA-binding mutant reporter in which G46:C74 was changed to C:G (Tan et al., 1993).

e. Glutamine-mediated Binding Specificity

Figure 8B:
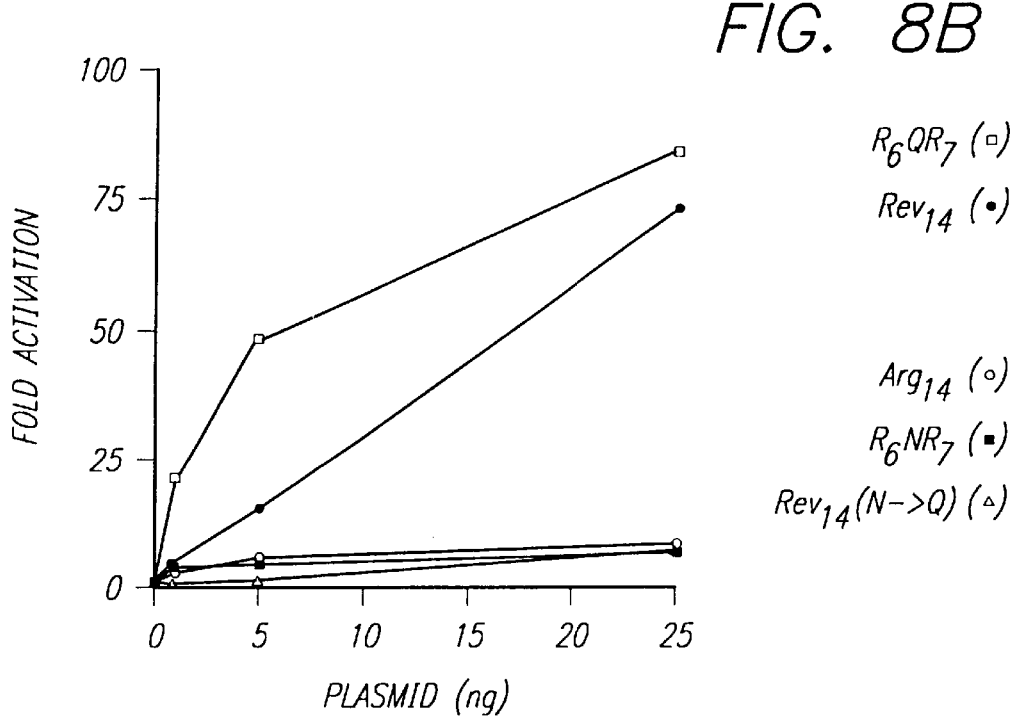

Most of the selected RRE binders contained at least one glutamine residue, most often located at a position corresponding to Asn40 of Rev. This was especially surprising given the recent report of a change of specificity Rev mutant in which Asn40→Gln allowed recognition of a mutant RRE IIB site containing an A73→G substitution but abolished binding to the wild-type site (Jain et al., 1996). In the Rev peptide-RRE IIB complex, Asn40 hydrogen bonds to a non-Watson-Crick G47- A73 base pair (Battiste et al., 1996; Ye et al., 1996). Upon examining the sequences of the selected glutamine-containing peptides (FIG. 7), we observed that the other non-arginine residues were rather variable and therefore suspected that glutamine within a polyarginine context might be sufficient to mediate high-affinity RRE binding. We constructed a variant ,R6QR7, in which glutamine was placed at the equivalent of position 40 in an otherwise all-arginine background and measured activation of the RREIIB-CAT reporter. Remarkably, this variant was substantially more active than the Rev peptide, and equally remarkable, a variant containing asparagine at the same position, R6NR7, was inactive (FIG. 8B). The opposite result was obtained in the context of the Rev sequence; the wild-type peptide, which contains asparagine, was active whereas the glutamine mutant was inactive, as reported by Jain et al, 1996). Thus, the context in which asparagine or glutamine is presented to the RRE is critical.

The arginine-rich RNA-binding motif, first identified in bacteriophage antiterminator proteins, ribosomal proteins, and several retroviral proteins including HIV Tat and Rev (Lazinski et al., 1989), appears to provide an excellent framework for designing novel RNA-binding molecules. Here we have explored the hypothesis that specific binders can be readily evolved from a polyarginine peptide by screening a combinatorial library in which four positions were randomized within a sequence of fourteen arginines. We identified several peptides that bind tightly to the RRE and found that a single glutamine within a polyarginine framework mediated tight binding.

In the Rev peptide, which binds to the major groove of the RRE IIBsite in an a-helical conformation (Tan et al., 1993; Battiste et al., 1996; Ye et al., 1996), Asn40 makes a specific contact to a G47-A73 base pair, with its amide group donating a hydrogen bond to the N7 group of G47 and accepting a hydrogen bond from the N6 group of A73. We propose that the amide group of glutamine makes a similar contact to the G-A pair in the selected peptides. Remarkably, no RRE-binding activity was observed when glutamine was replaced by asparagine in the polyarginine context, and conversely, no activity was observed when asparagine was replaced by glutamine in the Rev peptide context. The orientation and depth of penetration of the Rev a-helix in the major groove is determined by a set of contacts to functional groups on the bases and to backbone groups, with several contacts involving arginine side chains. Clearly, the Rev-RRE arrangement accommodates the coplanar orientation between Asn40 and the G-A pair, and we infer that the extra methylene group of glutamine cannot be accommodated. In contrast, in the polyarginine context we imagine that the peptide remains helical but is oriented less deeply in the major groove, perhaps because additional arginines cannot be accommodated at the tight RNA-peptide interface or because additional contacts are made, and glutamine has the appropriate length to contact the G-A pair. The observation that the glutamine-containing peptides bind more tightly than the Rev peptide suggests that the presumed new orientation may be more energetically favorable. Detailed structural information is clearly needed to establish the basis for improved binding. In DNA-protein interactions, coplanar amino acid-base arrangements are commonly seen in which arginines form two hydrogen bonds to the guanines of G:C base pairs and glutamine or asparagine form two hydrogen bonds to the adenines of A:T pairs, as originally proposed by Seeman et al., 1976. It appears that glutamine or asparagine side chains are also well-suited to form coplanar hydrogen-bonded interactions with G-A base pairs, which may be common to RNA structures (Wyatt et al., 1993). An Asn40→Gln mutation was identified in Rev as a change of specificity mutant that bound a mutant RRE (A73→G)with high affinity but did not bind the wild-type RRE (Jain et al., 1996), consistent with our results. Since the G-A pair is mutated, it seems reasonable that glutamine docks differently to this mutant RRE site.

Arginine-rich peptides with different sequences and conformations than Rev have been identified that bind to specifically RRE IIB and these have been evolved into tighter binders than Rev. RNA aptamers have been identified by in vitro selection that bind Rev with 10-fold higher affinities than IIB (Symensma et al., 1996). Apparently the affinity of the Rev peptide-RRE IIB interaction has not been optimized during viral evolution. Since Rev is essential for HIV replication and Rev binding to the RRE is essential for function, tight RRE-binding peptides might be used to block the interaction and thereby inhibit viral replication. Preliminary experiments suggest that Rev function can be inhibited by the peptides described here, possibly providing new leads for drug discovery. The mammalian screening system may be viewed as a tool to help identify interesting and potentially useful RNA-binding molecules.

BIBLIOGRAPHY

1. Allen et al. (1995). Finding prospective partners in the library: the two-hybrid system and phage display find a match. *Trends Biochem. Sci.* 20:511–516.
2. Battiste et al. (1996). Alpha helix major groove recognition in an HIV-1 Rev peptide-RRE RNA complex. *Science* 273:1547–1551.
3. Calnan et al. (1991). Analysis of arginine-rich peptides from the HIV Tat protein reveals unusual features of RNA-protein recognition. *Genes Dev* 5:201–10.
4. Chen et al. (1994). An RNA-binding peptide from bovine immunodeficiency virus Tat protein recognizes an unusual RNA structure. *Biochemistry* 33:2708–15.
5. Clackton et al. (1994). In vitro selection from protein and peptide libraries. *Trends Biotechnol.* 12:173–184.
6. Clewell (1972. Nature of Col E1 plasmid replication in *Escherichia coli* in the presence of chloramphenicol. *J. Bact.* 110:667–676.
7. Cormack et al. (1996). FACS-optimized mutants of the green fluorescent protein (GFP). *Gene* 173:33–38.
8. Cubitt et al. (1995). Understanding, improving and using green fluorescent proteins. *Trends Biochem, Sci.* 20:448–455.
9. Dang et al. (1989). Nuclear and nucleolar targeting sequences of cerb-A, c-myb, N-myc, p53, HSP70, and HIV tat proteins. *J Biol Chem* 264:18019–23.
10. Feinberg et al. (1991). The role of Tat in the human immunodeficiency virus life cycle indicates a primary effect on transcriptional elongation. *Proc Natl Acad Sci USA* 88:4045–9.
11. Felgner et al. (1987). Lipofection: a highly efficient, lipid-mediated DNA-transfection procedure. *Proc Natl Acad Sci USA* 84:7413–7.
12. Fouts et al. (1996). Improved method for selecting RNA-binding activities in vivo. *Nucleic Acids Res* 24:1582–4.
13. Frankel et al. (1988). Cellular uptake of the tat protein from human immunodeficiency virus. *Cell* 55:1189–93.
14. Haas et al. (1996). Codon usage limitation in the expression of HIV-1 envelope glycoprotein. *Curr. Biol.* 6:315–324.
15. Harada et al. (1997). In vivo selection of specific RNA-binding polypeptides using a transcription antitermination reporter assay. In *RNA-Protein Interactions: A Practical Approach*, C. Smith, eds. (Oxford: Oxford University Press).
16. Harada et al. (1996). Selection of RNA-binding peptides in vivo. *Nature* 380:175–9.
17. Hauber et al. (1989). Mutational analysis of the conserved basic domain of human immunodeficiency virus tat protein. *J Virol* 63:1181–7.
18. Hirt (1967). Selective extraction of polyoma DNA from infected mouse cell cultures. *J. Mol. Biol.* 26:365–369.
19. Jain et al. (1996). A structural mo&l for the HIV-1 Rev-RRE complex deduced from altered-specificity rev variants isolated by a rapid genetic strategy. *Cell* 87:115–125.
20. Kao et al. (1987). Anti-termination of transcription within the long terminal repeat of HIV-1 by tat gene product. *Nature* 330:489–93.
21. Kato et al. (1992). HIV-1 Tat acts as a processivity factor in vitro in conjunction with cellular elongation factors. *Genes Dev* 6:655–66.
22. Kinsella et al. (1996). Episomal vectors rapidly and stably produce high-titer recombinant retrovirus. *Hum. Gene. Ther.* 7:1405–1413.
23. Kitamura et al. (1995). Efficient screening of retroviral cDNA expression libraries. *Proc. Natl. Acad. Sci. USA* 92:9146–9150.
24. Laird-Offringra et al. (1995). Analysis of RNA-binding proteins by in vitro genetic selection: Identification of an amino acid residue important for locking U1A onto its RNA target. *Proc. Natl. Acad. Sci. USA* 92:11859–11863.
25. Laspia et al. (1993). HIV-1 Tat overcomes inefficient transcriptional elongation in vitro. *J Mol Biol* 232:732–46.
26. Lazinski et al. (1989). Sequence-specific recognition of RNA hairpins by bacteriophage antiterminators requires a conserved arginine-rich motif. *Cell* 59:207–18.
27. Marciniak et al. (1991). HIV-1 Tat protein promotes formation of more processive elongation complexes. *Embo J* 10:4189–96.
28. Martin et al. (1997). The gene for histone RNA hairpin binding protein is located on chromosome 4 and encodes a novel type of RNA hairpin binding protein. *EMBO J.* 16:769–778.
29. Mermer et al. (1990). Identification of transdominant HIV-1 rev protein mutants by direct transfer of bacterially produced proteins into human cells. *Nucleic Acids Res* 18:2037–44.
30. Oubridge et al. (1994). Crystal structure at 1.92 A resolution of the RNA-binding domain of the U1A spliceosomal protein complexed with an RNA hairpin. *Nature* 372:432–438.
31. Pachnis et al. (1990). Transfer of a yeast artificial chromosome carrying human DNA from Saccharomyces cerevisiae into mammalian cells. *Proc. Natl. Acad. Sci. USA* 87:5109–5113.
32. Parada et al. (1996). Enhanced processivity of RNA polymerase II triggered by Tat-induced phosphorylation of its carboxy-terminal domain. *Nature* 384:375–378.
33. Puglisi et al. (1995). Solution structure of a bovine immunodeficiency virus Tat-TAR peptide-RNA complex. *Science* 270:1200–1203.
34. Qian et al. (1993). Cloning of a cDNA encoding an RNA binding protein by screening expression libraries using a Northwestern strategy. *Anal. Biochem.* 212:547–554.
35. Rassoulzadegan et al. (1982). High frequency of gene transfer after fusion between bacteria and eukaryotic cells. *Nature* 295:257–259.
36. Rosen et al. (1985). The location of cis-acting regulatory sequences in the human T cell lymphotropic virus type III (HTLV-III/LAV) long terminal repeat. *Cell* 41:813–23.
37. Roy et al. (1990). A bulge structure in HIV-1 TAR RNA is required for Tat binding and Tat-mediated trans-activation. *Genes Dev* 4:1365–73.
38. Ruben et al. (1989). Structural and functional characterization of human immunodeficiency virus tat protein. *J Virol* 63:1–8.
39. Sandri-Goldin et al. (1981). High-frequency transfer of cloned herpes simplex virus type 1 sequences to mammalian cells by protoplast fusion. *Mol. Cell. Biol.* 1:743–752.
40. Schaffner (1980). Direct transfer of cloned genes from bacteria to mammalian cells. *Proc. Natl. Acad. Sci. USA* 77:2163–2167.
41. Seed (1995). Developments in expression cloning. *Curr. Op. Biotechnol.* 6:567–573.
42. Seed (1987). Molecular cloning of the CD2 antigen, the T-cell erythrocyte receptor, by a rapid immunoselection procedure. *Proc. Natl. Acad. Sci. USA* 84:3365–3369.
43. Seeman et al. (1976). Sequence-specific recognition of double helical nucleic acids by proteins. *Proc. Natl. Acad. Sci. USA* 73:804–808.
44. Selby et al. (1990). Trans-activation by HIV-1 Tat via a heterologous RNA binding protein. *Cell* 62:769–76.
45. SenGupta et al. (1996). A three-hybrid system to detect RNA-protein interactions in vivo. *Proc. Natl. Acad. Sci. USA* 93:8496–8501.
46. Southgate et al. (1990). Activation of transcription by HIV-1 Tat protein tethered to nascent RNA through another protein. *Nature* 345:640–2.
47. Southgate et al. (1991). The HIV-1 Tat protein activates transcription from an upstream DNA-binding site; implications for Tat function. *Genes Dev* 5:2496–507.
48. Symensma et al. (1996). RNA aptamers selected to bind human immunodeficiency virus type 1 Rev in vitro are Rev responsive in vivo. *J Virol* 70:179–187.
49. Tan et al. (1993). RNA recognition by an isolated alpha helix. *Cell* 73:1031–1040.
50. Tan et al. (1994). Costabilization of peptide and RNA structure in an HIV Rev peptide-RRE complex. *Biochemistry* 33:14579–14585.
51. Tan et al. (1995). Structural variety of arginine-rich RNA-binding peptides. *Proc Natl Acad Sci USA* 92:5282–5286.
52. Wang et al. (1996). The protein that binds the 3' end of histone mRNA: a novel RNA-binding protein required for histone pre-mRNA processing. *Genes Dev* 10:3028–3040.
53. Wilhelm et al. (1996). A one-hybrid system for detecting RNA-protein interactions. *Genes to Cells* 1:317–323.
54. Wyatt et al. (1993). RNA structural elements and RNA function. In *The RNA World*, R. F. Gestaland, and Atkins, J. F., eds. (cold Spring Harbor, N.Y.: Cold Spring Harbor, N.Y.: Cold Spring Harbor Laboratory Press).
55. Yang et al. (1996). The human immunodeficiency virus Tat proteins specifically associate with TAK in vivo and require the carboxyl-terminal domain of RNA polymerase II for function. *J Virol* 70:4576–4584.
56. Yates et al. (1985). Stable replication of plasmids derived from Epstein-Barr virus in various mammalian cells. *Nature* 313:912–815.
57. Ye et al. (1996). Deep penetration of an alpha-helix into a widened RNA major groove in the HIV-1 rev peptide-RNA aptamer complex. *Nat Struc Biol* 3:1026–1033.
58. Ye et al. (1995). Molecular recognition in the bovine immunodeficiency virus Tat peptide-TAR RNA complex. *Chem Biol* 2:827–940.

59. Zhou et al. (1996). Tat-SF1: Cofactor for stimulation of transcriptional elongation by HIV-1 Tat. *Science* 274:605–610.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

What is claimed is:

1. A method of screening a library of nucleic acid fragments in eucaryotic cells, comprising:
   (1) transforming the library of nucleic acid fragments into primary cells, wherein the cells are procaryotic or fungi;
   (2) culturing the primary cells under conditions whereby the copy number of nucleic acid fragments is amplified to an average of at least 200 copies per transformed cell;
   (3) contacting the transformed primary cells with a population of eucaryotic cells, which lack capacity for episomal replication of the transferred nucleic acid fragments, under conditions whereby outersurfaces of the transformed primary cells and eucaryotic cells fuse and contents of the transformed primary cells including at least some of the library of nucleic acid fragments are transferred to the eucaryotic cells;
   (4) screening the nucleic acid fragments in the eucaryotic cells to isolate one or more eucaryotic cells having a desired property conferred by one or more members of the library of nucleic acid fragments, an expression product thereof, or a secondary metabolite of an expression product;
   (5) lysing the one or more eucaryotic cells to release the one or more members of the library of nucleic acid fragments and electroporating the nucleic acid fragments into further procaryotic cells;
   (6) propagating the further procaryotic cells to amplify the one or more members of the library of nucleic acid fragments, which confer the desired property.

2. The method of claim 1, wherein the primary cells are *E. coli*, the nucleic acid fragments are contained in a ColE1 vector, and the primary cells are cultured in the presence of an antibiotic to amplify the copy number of the library of nucleic acid fragments.

3. The method of claim 1, further comprising isolating a nucleic acid fragment from the amplified further procaryotic cells, which confers the desired property.

4. The method of claim 1, further comprising repeating steps (2)–(5), wherein the amplified further procaryotic cells in step (5) of a previous cycle form the transformed primary cells in step (2) of the next cycle.

5. The method of claim 1, wherein the library of nucleic acid fragments has at least $10^5$ members.

6. The method of claim 1, wherein at least ten different members of the library of nucleic acid fragments are electroporated from the one or more eucaryotic cells to the further procaryotic cells.

7. The method of claim 1, wherein the library of nucleic acid fragments are expressed in the eucaryotic cells before the screening.

8. The method of claim 1, wherein the nucleic acid fragments encode different peptides, and one or more of the peptides confers the desired property in the eucaryotic cells.

9. The method of claim 1, wherein the nucleic acid fragments encode enzymes, which produce secondary metabolites in the procaryotic cells, which are transferred together with at least some of the nucleic acid fragments to the eucaryotic cells, and one or more of the secondary metabolites confers the desired property in the eucaryotic cells.

10. The method of claim 8, wherein, in the screening step, the eucaryotic cells contain a construct encoding a reporter enzyme operably linked to a regulatory sequence, and the one or more peptides confers the desired property by binding to the regulatory sequence or a transcript thereof inducing expression of the reporter enzyme.

11. The method of claim 10, wherein the transformed primary cells comprise the construct which is transferred into the eucaryotic cells with the library of nucleic acid fragments.

12. The method of claim 10, wherein the reporter is GFP.

13. The method of claim 11, wherein a transcript of the regulatory sequence is recognized by a site-specific RNA binding peptide and the nucleic acid fragments encode the RNA binding peptide.

14. The method of claim 13, wherein the nucleic acid fragments encode fusion proteins comprising an RNA binding peptide and a transcriptional inducer, the RNA binding peptide differing among fusion proteins.

15. The method of claim 14 wherein the construct encodes GFP operably linked to a promoter induced by HIV-1 TAT and an RNA binding site and the transcriptional inducer is a HIV-1 TAT polypeptide.

16. The method of claim 3, further comprising determining the sequence of the isolated member of the nucleic acid fragment library.

17. The method of claim 16, further comprising producing the expression product of the isolated member of the nucleic acid fragment library.

18. The method of claim 17, further comprising formulating the expression product as a therapeutic composition.

19. The method of claim 1, wherein the nucleic acid fragments are members of a natural library.

20. The method of claim 1, wherein the nucleic acid fragments are members of a randomized library.

21. A method of screening a library of nucleic acid fragments in eucaryotic cells, comprising:
   (1) transforming the library of nucleic acid fragments into primary cells, wherein the cells are procaryotic or fungi;
   (2) contacting the transformed primary cells with a population of eucaryotic cells under conditions whereby outersurfaces of the transformed primary cells and eucaryotic cells fuse and contents of the transformed primary cells including at least some of the library of nucleic acid fragments are transferred to the eucaryotic cells;
   (3) screening the nucleic acid fragments in the eucaryotic cells without substantial replication of the nucleic acid fragments in the eucaryotic cells to isolate one or more eucaryotic cells having a desired property conferred by one or more members of the library of nucleic acid fragments, an expression product thereof, or a secondary metabolite of an expression product;

(4) transferring the one or more members of the library of nucleic acid fragments into further procaryotic cells;

(6) propagating the further procaryotic cells to amplify the one or more members of the library of nucleic acid fragments, which confer the desired property.

22. A method of screening a library of nucleic acid fragments in eucaryotic cells, comprising:

(1) transforming the library of nucleic acid fragments into cells, wherein the cells are procaryotic cells or fungi, and culturing the cells under conditions in which expression products and/or secondary metabolites of expression products are produced;

(2) contacting the transformed cells with a population of eucaryotic cells under conditions whereby outersurfaces of the transformed procaryotic and eucaryotic cells fuse and contents of the transformed procaryotic cells including at least some of the library of nucleic acid fragments, expression products thereof and/or secondary metabolites of expression products are transferred to the eucaryotic cells, whereby at least some eucaryotic cells receive an expression product and/or a secondary metabolite thereof and a nucleic acid fragment encoding the expression product;

(3) screening the eucaryotic cells to isolate one or more eucaryotic cells having a desired property conferred by one or more of the expression products or one or more of the secondary metabolites produced in the primary cells;

(4) transforming the one or more member of the library of nucleic acid fragments from the one or more eucaryotic cells into further procaryotic cells;

(5) propagating the transformed further procaryotic cells to amplify the one or more members of the library of nucleic acid fragments, which produce the one or more expression products and/or one or more secondary metabolites that confer the desired property.

23. A method of screening for RNA binding peptides in a eucaryotic cells, comprising:

introducing into a population of eucaryotic cells a library of nucleic acid fragments encoding fusion proteins; a fusion protein comprising a peptide linked to a transcriptional inducer, the peptides varying between fusion proteins;

wherein the eucaryotic cells further comprise a construct encoding a reporter gene operably linked to a promoter from which expression is stimulated by the transcriptional inducer and an RNA binding site;

whereby one or more fusion proteins, each comprising a peptide having specific affinity for the RNA binding site bind to the RNA binding site of the reporter construct or a transcript thereof via the peptide, and the transcriptional inducer linked to the peptide stimulates expression of the reporter gene from the promoter;

isolating one or more eucaryotic cells with stimulated expression of the reporter gene, the one or more cells containing one or more nucleic acid fragments encoding the one or more fusion proteins comprising a peptide having specific affinity for the RNA binding site wherein the introducing step comprises:

(1) transforming the library of nucleic acid fragments into primary cells, which are procaryotic cells or fungi;

(2) contacting the transformed primary cells with the population of eucaryotic cells under conditions whereby outersurfaces of the transformed primary and eucaryotic cells fuse and contents of the transformed primary cells including at least some of the library of nucleic acid fragments are transferred to the eucaryotic cells; and the method further comprises (3) transforming nucleic acid fragments from the isolated one or more eucaryotic cells into further procaryotic cells;

(4) propagating the transformed further procaryotic cells to amplify one or more members of the library of nucleic acid fragments encoding fusion proteins comprising a peptide with a specific affinity for the RNA binding site.

24. The method of claim 23, wherein the primary cells are E. coli, the nucleic acid fragments are contained in a ColE1 vector, and the primary cells are cultured in the presence of an antibiotic to amplify the copy number of the library of nucleic acid fragments.

25. The method of claim 24, wherein the eucaryotic cells lack capacity for episomal replication of the transferred nucleic acid fragments.

26. The method of claim 23, wherein the transcriptional inducer is a HIV TAT polypeptide and the promoter is a HIV LTR promoter.

27. The method of claim 26, wherein the RNA binding site is a HIV RRE site.

28. The method of claim 27, wherein the HIV TAT polypeptide lacks a natural HIV Tat RNA binding domain.

29. The method of claim 23, wherein the construct is transferred to the eucaryotic cells as a component of the contents of the primary cells.

30. The method of claim 23, further comprising formulating synthesizing the peptide having specific affinity for the RNA binding site.

31. The method of claim 23, further comprising formulating the peptide having specific affinity for the RNA binding site in a therapeutic or diagnostic composition.

32. A method of screening RNA sequences for specific affinity to a selected peptide in eucaryotic cells, comprising:

introducing into a population of eucaryotic cells a library of variant forms of a first construct, the first construct encoding a reporter gene operably linked to a promoter from which expression is stimulated by a transcriptional inducer and a potential RNA binding site, which varies between the variant forms;

wherein the eucaryotic cells further comprise a second construct encoding a fusion protein comprising a transcriptional inducer linked to the selected peptide;

whereby the fusion protein binds to one or more variant forms of the first construct or transcripts thereof, each having a potential RNA binding site with specific affinity for the peptide, stimulating expression of the reporter gene from the promoter;

isolating one or more eucaryotic cells with stimulated expression of the reporter gene, the one or more cells containing one or more variant forms of the first construct encoding one or more potential RNA binding sites with specific affinity for the selected peptide.

33. The method of claim 21, wherein the nucleic acid fragments are not expressed in the eucaryotic cells.

* * * * *

```
                           SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
         (A) LENGTH: 23 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:1:

Ala Ala Ala Ala Thr Arg Gln Ala Arg Arg Asn Arg Arg Arg Arg
1               5                  10                  15

Arg Arg Ala Ala Ala Ala Arg
            20

(2) INFORMATION FOR SEQ ID NO:2:

(i) SEQUENCE CHARACTERISTICS:
         (A) LENGTH: 23 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:2:

Ala Ala Ala Ala Arg Arg Arg Arg Arg Arg Arg Arg Arg Arg Arg
1               5                  10                  15

Arg Arg Ala Ala Ala Ala Arg
            20

(2) INFORMATION FOR SEQ ID NO:3:

(i) SEQUENCE CHARACTERISTICS:
         (A) LENGTH: 23 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 5
         (D) OTHER INFORMATION: /product= "OTHER"
             /note= "Xaa = Gln, Arg, Thr, Asn, Ala,
             Gly, Pro, His, Lys, Ser, Asp or Glu"

(ix) FEATURE:
         (A) NAME/KEY: Modified-site
         (B) LOCATION: 7..8
         (D) OTHER INFORMATION: /product= "OTHER"
             /note= "Xaa = Gln, Arg, Thr, Asn, Ala,
             Gly, Pro, His, Lys, Ser, Asp or Glu"

(ix) FEATURE:
         (A) NAME/KEY: Modified-site
         (B) LOCATION: 11
```

```
            (D) OTHER INFORMATION: /product= "OTHER"
                /note= "Xaa = Gln, Arg, Thr, Asn, Ala,
                Gly, Pro, His, Lys, Ser, Asp or Glu"

(xi) SEQUENCE DESCRIPTION: SEQ ID NO:3:

Ala Ala Ala Ala Xaa Arg Xaa Xaa Arg Arg Xaa Arg Arg Arg Arg
1               5                   10                  15

Arg Arg Ala Ala Ala Ala Arg
            20

(2) INFORMATION FOR SEQ ID NO:4:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Ala Ala Ala Ala Arg Arg Arg His Arg Arg Gln Arg Arg Arg Arg
1               5                   10                  15

Arg Arg Ala Ala Ala Ala Arg
            20

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Ala Ala Ala Ala Gly Arg Arg Arg Arg Arg Gln Arg Arg Arg Arg
1               5                   10                  15

Arg Arg Ala Ala Ala Ala Arg
            20

(2) INFORMATION FOR SEQ ID NO:6:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Ala Ala Ala Ala Gly Arg Arg Ala Arg Arg Arg Arg Arg Arg Arg
1               5                   10                  15

Gln Ser Cys Arg Arg Lys Met Thr Arg Asp
            20                  25

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide
```

-continued (xi) SEQUENCE DESCRIPTION: SEQ ID NO:7:

Ala Ala Ala Ala Arg Arg Arg Glu Arg Arg Arg Arg Arg Arg Arg Arg
1               5                   10                  15

Gln Ser Cys Arg Arg Lys Met Thr Arg Asp
            20                  25

(2) INFORMATION FOR SEQ ID NO:8:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Ala Ala Ala Ala Gly Arg Gln Gly Arg Arg Arg Arg Arg Arg Arg Arg
1               5                   10                  15

Gln Ser Cys Arg Arg Lys Met Thr Arg Asp
            20                  25

(2) INFORMATION FOR SEQ ID NO:9:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Ala Ala Ala Ala Gly Arg Arg Arg Arg Gln Arg Arg Arg Arg
1               5                   10                  15

Arg Lys Leu Pro Pro Gln Asp Asp Ser Arg Leu Val Asp Pro Asp Pro
            20                  25                  30

Pro Gly Phe Ser Val
        35

(2) INFORMATION FOR SEQ ID NO:10:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Ala Ala Ala Ala Gln Arg Arg Arg Arg Gln Arg Arg Arg Arg
1               5                   10                  15

Arg Arg Ala Ala Ala Ala Arg
            20

(2) INFORMATION FOR SEQ ID NO:11:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Ala Ala Ala Ala Gln Arg Arg Lys Arg Arg Gln Arg Arg Arg Arg
1               5                   10                  15

Arg Arg Ala Ala Ala Ala Arg
            20
```

(2) INFORMATION FOR SEQ ID NO:12:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

```
Ala Ala Ala Ala Gly Arg Ser Ala Arg Arg Asn Arg Arg Arg Arg
1               5                   10                  15

Arg Arg Ala Ala Ala Ala Arg
            20
```

(2) INFORMATION FOR SEQ ID NO:13:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
Ala Ala Ala Ala Gln Arg Arg Ala Arg Arg Gln Arg Arg Arg Arg
1               5                   10                  15

Arg Arg Ala Ala Ala Ala Arg
            20
```

(2) INFORMATION FOR SEQ ID NO:14:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

```
Ala Ala Ala Ala Ser Arg Arg Arg Arg Arg Gln Arg Arg Arg Arg
1               5                   10                  15

Arg Arg Ala Ala Ala Ala Arg
            20
```

(2) INFORMATION FOR SEQ ID NO:15:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Ala Ala Ala Ala Arg Arg Ala Lys Arg Asp Arg Arg Arg Arg Arg
1               5                   10                  15
```

```
Arg Arg Ala Ala Ala Ala Arg
            20

(2) INFORMATION FOR SEQ ID NO:16:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Ala Ala Ala Ala Arg Arg Gln Arg Arg Ala Arg Arg Arg Arg Arg
1               5                  10                  15

Arg Arg Ala Ala Ala Ala Arg
            20

(2) INFORMATION FOR SEQ ID NO:17:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Ala Ala Ala Ala Gly Arg Arg Gln Arg Arg Gln Arg Arg Arg Arg
1               5                  10                  15

Arg Arg Ala Ala Ala Ala Arg
            20

(2) INFORMATION FOR SEQ ID NO:18:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Ala Ala Ala Ala Gly Arg Arg Gln Arg Arg Arg Arg Arg Arg Arg
1               5                  10                  15

Arg Arg Ala Ala Ala Ala Arg
            20

(2) INFORMATION FOR SEQ ID NO:19:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

Ala Ala Ala Ala Arg Arg Arg Arg Arg Arg Gln Arg Arg Arg Arg
1               5                  10                  15

Arg Arg Ala Ala Ala Ala Arg
            20
```

(2) INFORMATION FOR SEQ ID NO:20:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

```
Ala Ala Ala Ala Gly Arg Lys Gly Arg Arg Glu Arg Arg Arg Arg
1               5                   10                  15

Arg Arg Ala Ala Arg Lys Met Thr Arg Asp
            20                  25
```

(2) INFORMATION FOR SEQ ID NO:21:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

```
Ala Ala Ala Ala Gly Arg Gly Glu Arg Arg Arg Arg Arg Arg Arg
1               5                   10                  15

Gln Ser Cys Arg Arg Lys Met Thr Arg Asp
            20                  25
```

(2) INFORMATION FOR SEQ ID NO:22:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
Ala Ala Ala Ala Gly Arg Glu Thr Arg Arg Gln Arg Arg Arg Arg
1               5                   10                  15

Gln Ser Cys Arg Arg Lys Met Thr Arg Asp
            20                  25
```

(2) INFORMATION FOR SEQ ID NO:23:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

```
ATCTCTTACG GCCGTGCCGC TGCAGCCVVK AGAVVKVVKA GGCGAVVKAG GAGACGGCGA      60

CGTCGCAGAG CTGCCGCCGC AAGATGACTC GAGACTAGTG GA                       102
```

(2) INFORMATION FOR SEQ ID NO:24:

(i) SEQUENCE CHARACTERISTICS:
        (A) LENGTH: 15 base pairs
        (B) TYPE: nucleic acid
        (C) STRANDEDNESS: single -continued (D) TOPOLOGY: linear (ii) MOLECULE TYPE: DNA (xi) SEQUENCE DESCRIPTION: SEQ ID NO:24:

TCCACTAGTC TCGAG								15